(12) United States Patent  
Guziak et al.

(10) Patent No.: US 7,162,926 B1  
(45) Date of Patent: Jan. 16, 2007

(54) LEAD EMBEDDED PRESSURE SENSOR

(75) Inventors: Robert Guziak, Thousand Oaks, CA (US); David Tory, Simi Valley, CA (US)

(73) Assignee: Kavlico Corporation, Moorpark, CA (US)

( * ) Notice: Subject to any disclaimer, the term of this patent is extended or adjusted under 35 U.S.C. 154(b) by 9 days.

(21) Appl. No.: 11/198,017

(22) Filed: Aug. 4, 2005

(51) Int. Cl.  
G01L 7/10 (2006.01)

(52) U.S. Cl. ..................................... 73/729.2

(58) Field of Classification Search ............. 73/722, 73/729.2, 706  
See application file for complete search history.

(56) References Cited

U.S. PATENT DOCUMENTS

| | | |
|---|---|---|
| 3,038,465 A | 6/1962 | Allard et al. |
| 3,631,850 A | 1/1972 | Levasseur |
| 3,943,915 A | 3/1976 | Severson |
| 4,016,764 A | 4/1977 | Rice |
| 4,023,562 A | 5/1977 | Hynecek et al. |
| 4,407,296 A | 10/1983 | Anderson |
| 4,485,813 A | 12/1984 | Anderson et al. |
| 4,683,757 A | 8/1987 | Adams et al. |
| 4,815,472 A | 3/1989 | Wise et al. |
| 4,854,326 A | 8/1989 | Merrick |
| 5,113,868 A | 5/1992 | Wise et al. |
| 5,257,630 A | 11/1993 | Broitman et al. |
| 5,564,434 A | 10/1996 | Halperin et al. |
| 5,755,668 A | 5/1998 | Itoigawa et al. |
| 5,836,886 A * | 11/1998 | Itoigawa et al. ............. 600/488 |
| 5,929,497 A * | 7/1999 | Chavan et al. ............... 257/417 |
| 6,109,113 A * | 8/2000 | Chavan et al. ................ 73/718 |
| 6,140,144 A * | 10/2000 | Najafi et al. .................. 438/53 |
| 6,394,986 B1 | 5/2002 | Millar |
| 6,454,720 B1 | 9/2002 | Clerc et al. |
| 6,460,234 B1 | 10/2002 | Gianchandani |
| 6,508,129 B1* | 1/2003 | Sittler .......................... 73/756 |
| 6,666,826 B1 | 12/2003 | Salo et al. |
| 6,855,115 B1 | 2/2005 | Fonseca et al. |
| 6,883,380 B1* | 4/2005 | Romo ......................... 73/729.2 |
| 6,890,300 B1 | 5/2005 | Lloyd et al. |
| 2001/0001311 A1 | 5/2001 | Park et al. |
| 2002/0115920 A1 | 8/2002 | Rich et al. |
| 2002/0151816 A1 | 10/2002 | Rich et al. |
| 2004/0138571 A1 | 7/2004 | Salo et al. |
| 2005/0015014 A1 | 1/2005 | Fonseca et al. |

* cited by examiner

*Primary Examiner*—Edward Lefkowitz  
*Assistant Examiner*—Andre Allen  
(74) *Attorney, Agent, or Firm*—Jeffer Mangels Butler & Marmaro, LLP

(57) ABSTRACT

A pressure capsule embedded in a pacemaker lead to monitor intracardiac chamber pressure is described. This pressure monitor capsule provides highly accurate pressure readings while insuring a high integrity seal against bodily fluids and tissue growth. The capsule is intended to be embedded into a pacemaker cardiac lead or a catheter with the distal (Tip) isolation diaphragm sensing pressure, coupling the pressure through an air column to a protected sensing MEMS device and providing a secure fluid seal to the lead walls. The proximal (Back) end of the capsule provides the electrical interface through the lead to the pacemaker pulse generator.

44 Claims, 22 Drawing Sheets

LEAD EMBEDDED PRESSURE SENSOR

FIELD OF THE INVENTION

This invention relates generally to intracardiac chamber pressure sensing and more particularly to pacemaker lead embedded pressure sensing mechanisms.

BACKGROUND OF THE INVENTION

Intracardiac blood pressure sensing for research, diagnostic and treatment dates back to the early part of the 20th century, where early investigations utilized a canula or needle-based system with a mercury manometer. Using these techniques, pressure fluctuations in all 4 chambers of the heart have been successfully monitored. Critical diagnostic measurements of right heart systolic (pumping) and diastolic (resting) pressures can indicate disease conditions such as mitrial valve stenosis (stiffening), pulmonary artery hypertension, right heart weakness following myocardial infarction (heart attack), peripheral venus return failure (reduced preload) and electrical anomalies (arrhythmia or conduction).

Blood pressure can be also monitored through a fluid-filled tube or catheter where a diaphragm in the tip of the catheter deflects to transfer pressure to a pressure sensor external to the body. This method is typically used in either canula-based or catheter-based pressure sensors. These sensors are typically Piezo Resistive Technology (PRT) sensors. In contrast, sensors based on a Wheatstone bridge topology require high power levels and are typically too large for implantation. In addition, the sensors typically need to send the signals back to a remote device to capture the measured signals, often subject to signal degradation in the transmission process.

Another blood pressure sensing technology is the fiber optic blood pressure sensor. The sensor works through a small cavity embedded in the sensor tip, where the blood pressure is measured by observing the changes in length of the cavity using a measurement based on white light interferometry. Sensing light is transmitted to and reflected back from the detecting diaphragm and cavity of the sensor tip via a multimode fiber.

Testing information has been published for capacitor diaphragm-based pressure sensors, coupled to pacemakers, where the sensors are an integral part of pacemaker leads. The sensors are typically implanted to monitor intracardiac right heart pressure and have demonstrated a high correlation to standard balloon catheter measurements. These devices use a capacitive-based sensor in a catheter or pacemaker lead having a titanium deflectable sensing diaphragm at the tip. The diaphragm acts as one plate of a sensing capacitor and inside the diaphragm is an air-filled cavity with a second capacitor plate. The value of the capacitance is inversely proportional to the plate distance. As the pressure changes, the titanium diaphragm deflects, changing the plate spacing and therefore the capacitance. This change in capacitance can be detected by an electronic circuit.

Capacitive sensors are based on the equation:

$$C = K \cdot (A/D)$$

where K is the dielectric constant, A is the capacitor plate area, and D is the distance between the 2 capacitor plates. With a metal diaphragm, the measurement of pressure is based on the plate deflection, or the change plate distance. Thus, the capacitance change per unit pressure is limited by the macroscopic motion of the plate. For high sensitivity, the plate movement must produce a significant capacitive change. This requires a thinner plate to allow the movement per unit pressure. However, reduced plate thickness complicates the diaphragm attachment method regardless of whether the diaphragm is welded, or adhesively bonded. Also, the capacitance of the wiring to separate electronics can be orders of magnitude greater than the diaphragm capacitance. This complicates the decoding electronics for pressure measurement. In addition, having the diaphragm directly contacting the sensing media (i.e., the liquid to be measured) can cause a shift of the capacitive value of the sensor from its initial nominal value. Thus, this design is susceptible to capative changes based on the sensing media with which it comes in contact.

Further, thermal effects, mechanical instability and aging effects contribute to an inaccuracy in the measurement taken by the capacitive-based sensor. For example, as the sensor ages, small movement in the wiring position or compression of the insulation may significantly alter the interconnect capacitance. This is seen as a change in the zero pressure reading or a drift of the reading with time. The range, accuracy and the repeatability of pressure measurement are not only limited by the motion of the diaphragm and the capacitance of the wiring, but also any thermally induced error. Since the diaphragm dimension can change by expansion and contraction due to thermal effects, accuracy is limited. The reproducibility of these thermal effects is also determined by the precision and reproducibility of the manufacturing process.

The current state of the art in intracardiac sensing is limited by the low level of signal output, remote sensing requirement, large physical size or custom fabrication for all designs. Most of the current state of the art sensors such as canula based, fluid filled catheters are not suitable for chronic (long term) unattended implantation. Others, such as the optical based sensors, require power levels too high for long term battery operation. Further, capacitor-based sensors require a secondary amplifier and detection circuit. These type of sensors may also be prone to long term drifting or lack of sensitivity.

SUMMARY OF THE PREFERRED EMBODIMENTS

The present invention solves the deficiencies of the existing systems by creating a pressure sensing (pressure sense) module in the form of a physically small, biologically inert package. It is intended for full implantation within the tip of a pacemaker lead or catheter. In accordance with one preferred embodiment of the present invention, the pressure sensing module is intended to be capable of chronic low power operation with high signal amplitude and long-term signal stability.

In one preferred embodiment of the present invention, a pressure sensing module includes a pressure sensing capsule having a body with a distal end and a proximal end, an electrical circuit integrated into the body, a first cavity located between the distal end and the proximal end, and an isolation diaphragm coupled to the distal end of the body. The pressure sensing module further includes a Mechanical Electrical Mechanical System (MEMS) pressure sensor mounted in the first cavity of the body of the pressure sensing capsule, and a second cavity for transferring a pressure applied to the isolation diaphragm to the MEMS pressure sensor.

In another embodiment, a pressure sensing capsule having a body with a distal end and a proximal end; an electrical circuit embedded into the body; a first cavity located between the distal end and the proximal end; and an isolation diaphragm coupled to the distal end of the body. The pressure sensing capsule further including a MEMS pressure sensor mounted in the first cavity of the body of the pressure sensing capsule; and, a pressure transfer cavity having a first opening operatively in communication with the isolation diaphragm and a second opening operatively in communication with the MEMS pressure sensor, the pressure transfer cavity transferring a pressure applied at the isolation diaphragm to the MEMS pressure sensor by transferring the pressure applied from the first opening to the second opening.

In another preferred embodiment, a method for creating a pressure sensing capsule includes the step of providing a body with a distal end and a proximal end, the body having a first cavity located between the distal end and the proximal end, an electrical circuit embedded into the body, and a pressure transfer cavity having a first opening operatively in communication with the isolation diaphragm and a second opening operatively in communication with the MEMS pressure sensor. The method further includes coupling an isolation diaphragm to the distal end of the body; sealing the isolation diaphragm around the first opening; and, sealing the MEMS pressure sensor to the second opening; wherein the first opening is operatively in communication with the isolation diaphragm and the second opening is operatively in communication with the MEMS pressure sensor.

Other objects, features, and advantages will become apparent to those skilled in the art from the following detailed description. It is to be understood, however, that the detailed description and specific examples, while indicating exemplary embodiments, are given by way of illustration and not limitation. Many changes and modifications within the scope of the following description may be made without departing from the spirit thereof, and the description should be understood to include all such modifications.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENT

Figure 1:
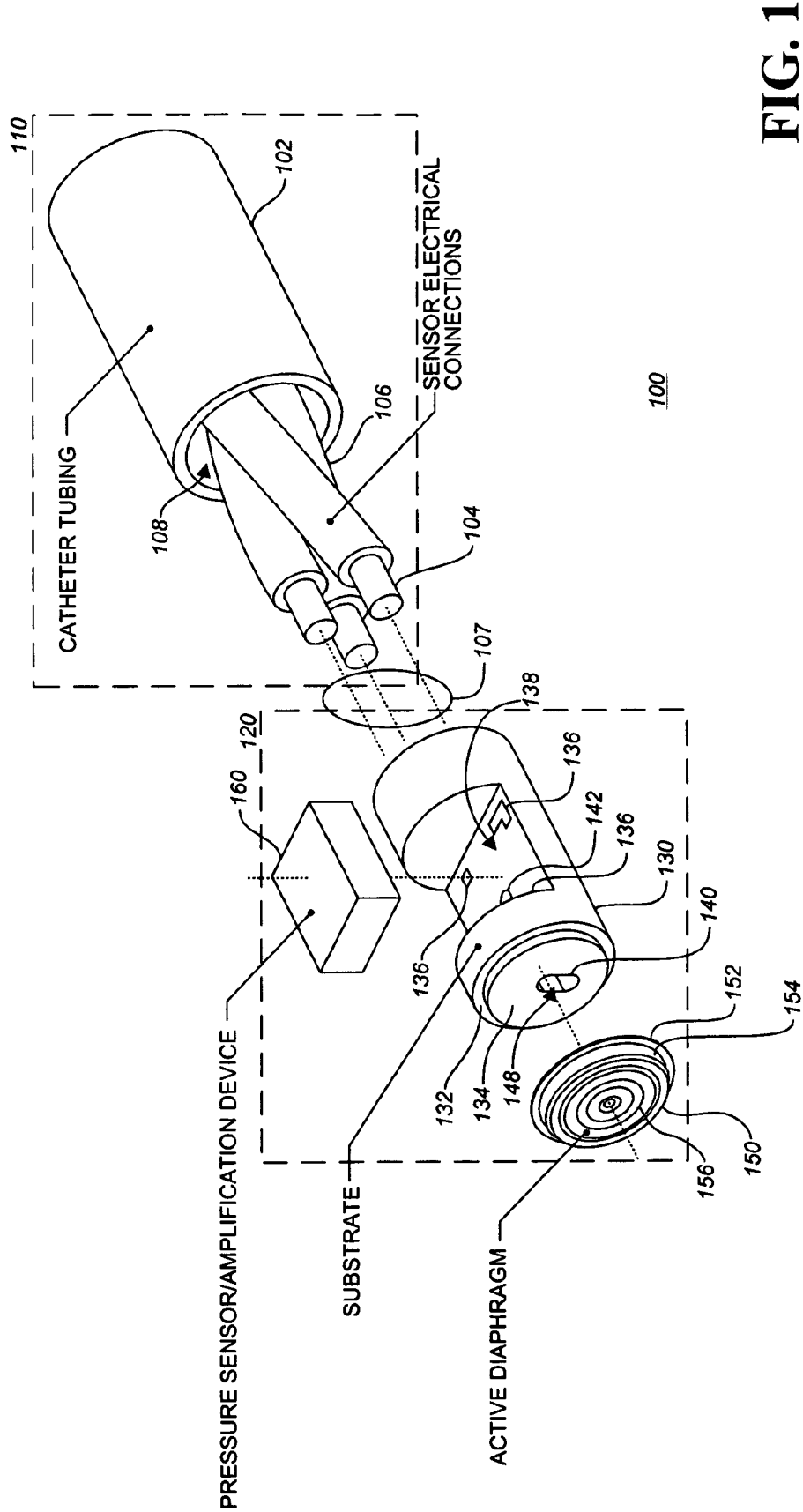
FIG. 1 is a perspective view of a pressure sensing module configured in accordance with a first preferred embodiment of the present invention.
Figure 2:
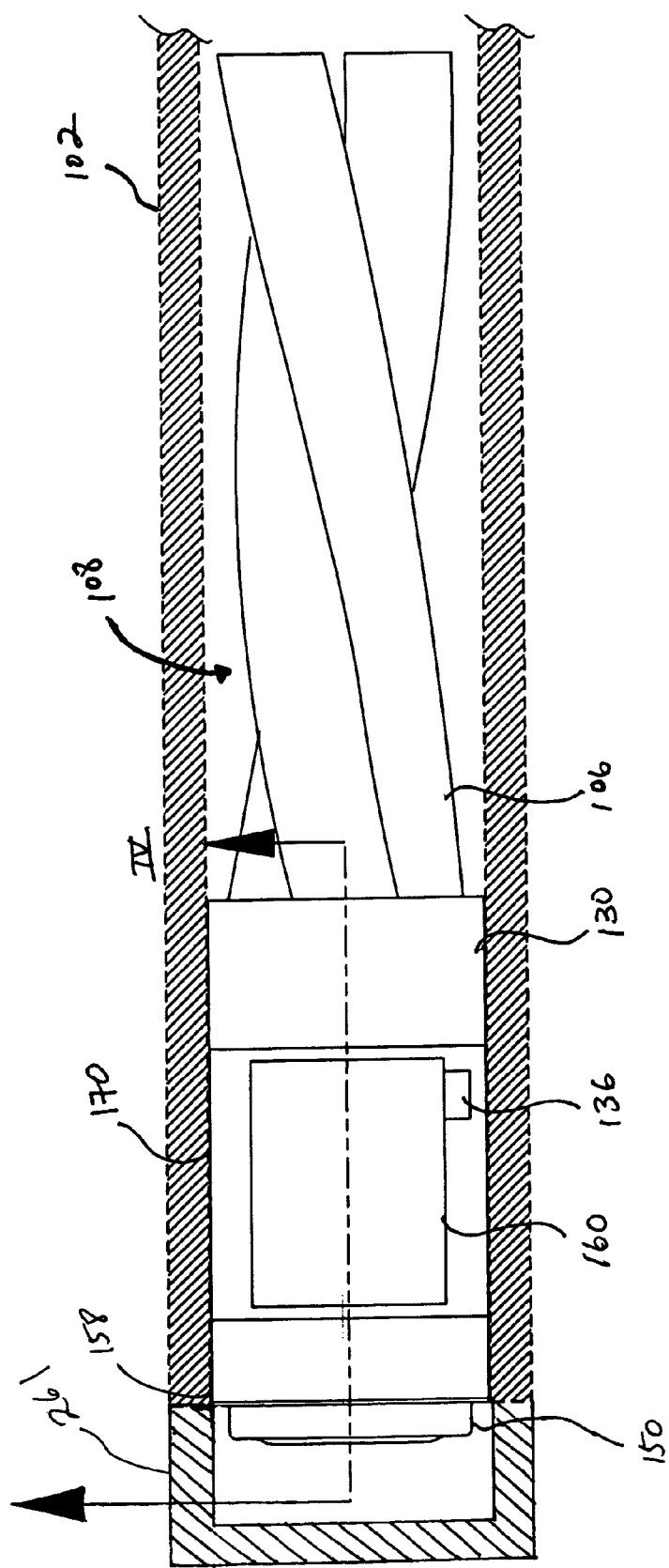
FIG. 2 is a top plan view of the pressure sensing module of FIG. 1.
Figure 3:
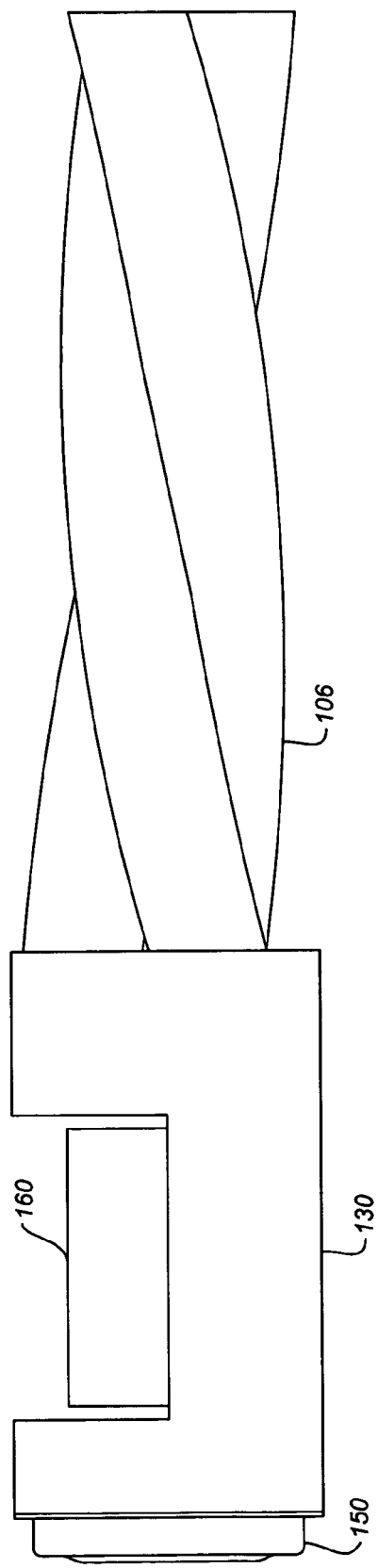
FIG. 3 is a side elevation view of the pressure sensing module of FIG. 1.

FIGS. 1–3 illustrate a pressure sensing module 120 configured in accordance with a preferred embodiment of the present invention. Pressure sensing (pressure sense) module 120 includes a pressure sensor capsule 130 that houses a Mechanical Electrical Mechanical System (MEMS) pressure sensor 160 (also referred to herein as a die), in a cavity 138 within its body. In one preferred embodiment of the present invention, the body of pressure sensor capsule 130 is constructed of a three-dimensional molded ceramic structure that supports the mounting of MEMS pressure sensor 160 in a lengthwise fashion to allow pressure sensor capsule 130 to achieve a form factor small enough to fit in a catheter tubing 102. This form factor should be small enough to fit leads used in a variety of configurations and applications, such as a pacemaker lead. It should be noted that the various descriptions for the mounting of pressure sensor module 120 to catheter tubing 102 in the various embodiments described herein are equally applicable to other lead configurations.

Figure 4:
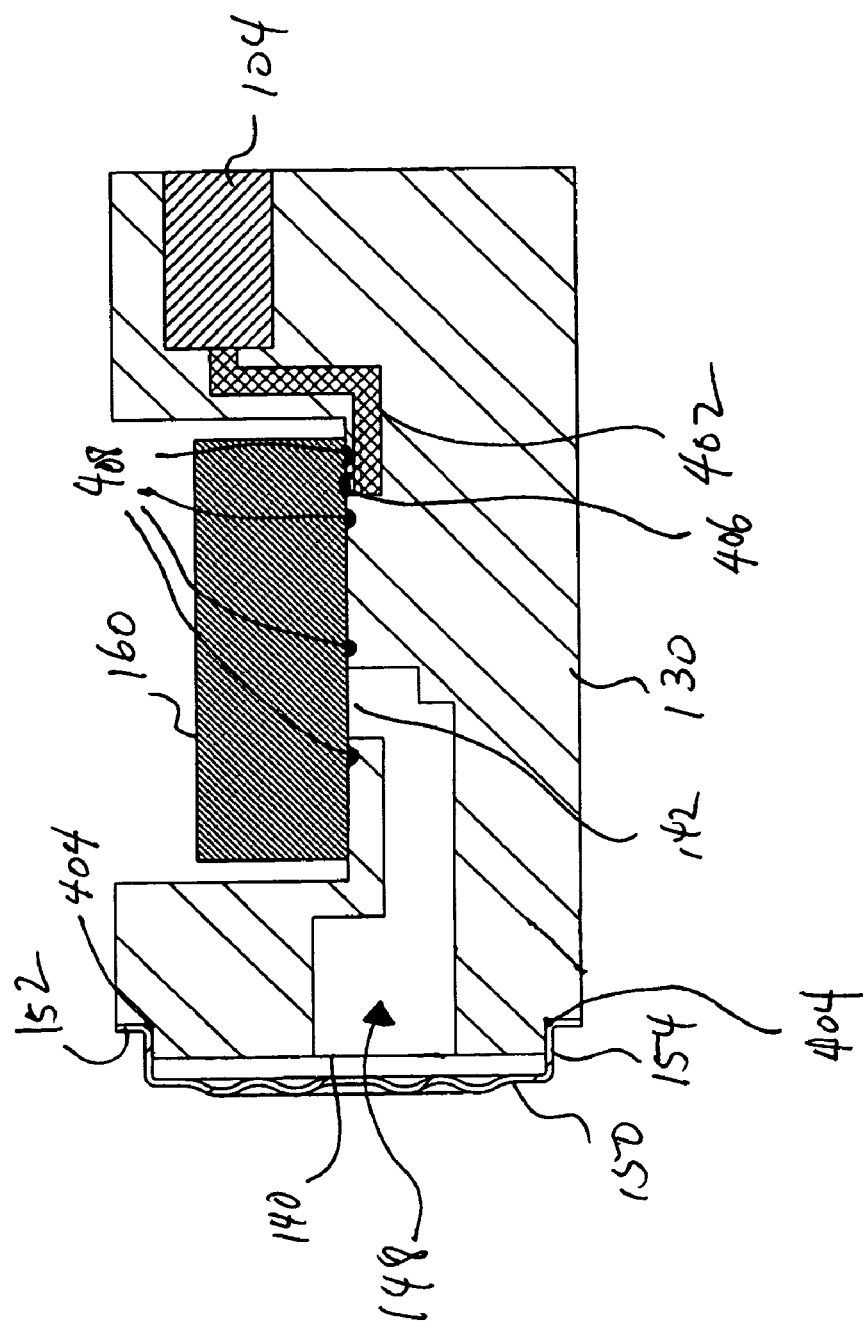
FIG. 4 is a cross-sectional view of the pressure sensing module of FIG. 1, taken along line IV—IV of FIG. 2.
Figure 5:
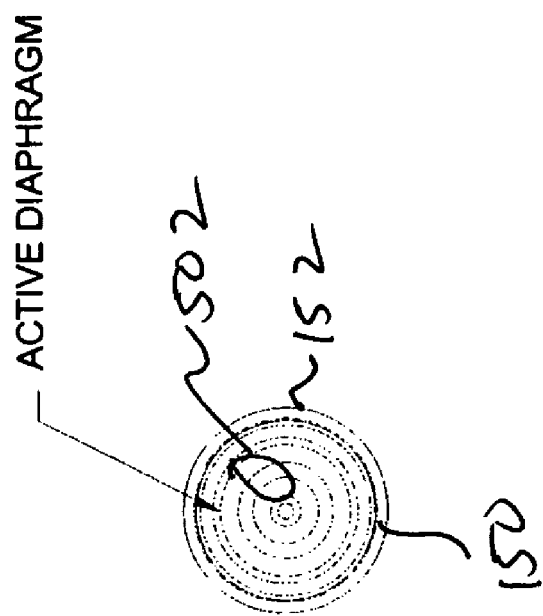
FIG. 5 is a front elevation view of the pressure sensing module of FIG. 1.

Pressure sensor capsule 130 includes an outer protrusion portion 134 to which an isolation diaphragm 150 is mounted. In one preferred embodiment of the present invention, isolation diaphragm 150 includes a raised portion 154 and a lip 152 mated to outer protrusion portion 134 and a shoulder 132, respectively. Pressure capsule 130 is secured to catheter tubing 102 through a combination of a laser weld at an outer circumference 158 of isolation diaphragm 150, and an adhesive support 170 that fills the gap between pressure sensor capsule 130 and catheter tubing 102. The "top hat" design of isolation diaphragm provides a flat surface (i.e., lip 152) where a connection to the ceramic structure occurs. A plurality of ridges and valleys, or corrugations, 156 provides strain relief and an extended range of linearity for a larger extent of diaphragm excursion for isolation diaphragm 150. As illustrated in FIG. 5, the top hat design also provides a means of isolating the pressure stress and the attachment stress because the flat center of sense area 502 of isolation diaphragm 150, is held against the ceramic structure, with no additional stress applied from the connection joint. Further, an additional feature included in this design is that a step in the shape of outer protrusion portion 134 is provided at the distal end of the capsule. As shown in FIG. 4, this step provides a space to contain a gel adhesive 404, which provides both a protective interface between the outer housing to pressure sensor capsule 130 and a way of presenting a smooth surface. Thus, the interface between isolation diaphragm 150 and the hard ceramic substrate of pressure sensor capsule 130 is protected by gel adhesive 404. In one preferred embodiment of the present invention, an adhesive such as Room Temperature Vulcanizing (RTV) rubber may be used as gel adhesive 404 to secure isolation diaphragm 150 to pressure sensor capsule 130. In other preferred embodiments of the present invention, epoxy, urethane, cyanoacrylic, or other suitably durable adhesive materials may be used as gel adhesive 404 to secure isolation diaphragm 150 to pressure sensor capsule 130. In yet other preferred embodiments of the present invention, attachment methods such as metal brazing of isolation diaphragm 150 to a metal (e.g., brass) insert in the ceramic structure of pressure sensor capsule 130 may be used. Pressure sensor capsule 130 may also include a protective tube 261 attached to isolation diaphragm 150 made from such materials as titanium or nitenol. Protective tube 261 may be a metal ring attached via a laser weld or a ring made from an adhesive such as RTV.

In one preferred embodiment of the present invention, MEMS pressure sensor 160 is attached in a flip chip attachment configuration. As further illustrated in FIG. 4, MEMS pressure sensor 160 does not directly contact the media to be measured outside pressure sensing module 120 as isolation diaphragm 150 isolates MEMS pressure sensor 160 from the media. In one preferred embodiment of the present invention, the pressure on isolation diaphragm 150 caused by the media is coupled to MEMS pressure sensor 160 through the pressure in an air filled pressure transfer cavity 148 located behind isolation diaphragm 150. Pressure transfer cavity 148 includes a diaphragm-side opening 140 that faces isolation diaphragm 150 and a pressure sensor-side opening 142 that faces a sensing diaphragm (not shown) of MEMS pressure sensor 160. Specifically, pressure transfer cavity 148 transfers the pressure sensed by isolation diaphragm 150 to the MEMS pressure sensor 160. In one preferred embodiment of the present invention, to minimize package size, pressure transfer cavity 148 is shaped to transfer the pressure received at diaphragm-side opening 140 from the center of isolation diaphragm 150 and route it beneath MEMS pressure sensor 160 before it appears at the sensor at pressure sensor-side opening 142. Thus, even though isolation diaphragm 150 is not directly facing the diaphragm of the MEMS pressure sensor 160, the system works as pressure is transferred by an air column from isolation diaphragm 150 to the capacitive sensor on the diaphragm opening portion of MEMS pressure sensor 160. In another preferred embodiment of the present invention, instead of air, an incompressible liquid such as oil may be used to fill pressure transfer cavity 148 and provide the transference of pressure. The incompressible liquid may include such liquids as silicon oil. In other preferred embodiments, including those described herein, the incompressible liquid may include other types of incompressible liquids and material. One benefit of using incompressible liquids instead of air is to reduce the amount of displacement by isolation diaphragm 150, which increases the linearity of the response of the sensor. The use of the incompressible liquid also increases the dynamic pressure range of the sensor. In one preferred embodiment, the liquid is introduced into pressure transfer cavity 148 via a liquid fill opening once isolation diaphragm 150 is sealed to pressure sensing module 130. The liquid fill opening may then be sealed using epoxy or other adhesive.

The chamber defined by pressure transfer cavity 148 is sealed by an underfill material 408 that surrounds pressure sensor-side opening 142 and provides a seal for a plurality of electrical solder bumps 406 that is used to attach, as well as provide electrical connection between, MEMS pressure sensor 160 and pressure sensor capsule 130. In one preferred embodiment, underfill material 408 is a specially engineered epoxy that is designed to both fill any undesired areas between MEMS pressure sensor 160 and pressure sensor capsule 130 and control the stress on the solder joints at the plurality of electrical bumps 406. The stress may be caused by either a difference in thermal expansion between MEMS pressure sensor 160 and pressure sensor capsule 130, or physical stresses caused by vibration or drop shock. Once cured, underfill material 408 absorbs the stress, reducing the strain on electrical bumps 406, greatly increasing the life of the finished package. Underfill material 408 is typically applied using a capillary flow process where material is dispensed next to a bonded flip chip such as MEMS pressure sensor 160 and allowed to "wick" under the die. The bumped MEMS device is placed in cavity 138 of pressure sensor capsule 130, with the sensing diaphragm (not shown) of MEMS pressure sensor 160 mated to pressure sensor-side opening 142. Thus, the underfill material seals the pressure within pressure transfer cavity 148 and provides stability for die attach and corrosion resistance.

As discussed above, in one preferred embodiment of the present invention, provisions for mounting MEMS pressure sensor 160 are made through solder bumping a plurality of contacts 136. Electrical coupling of MEMS pressure sensor 160 to external devices such as pacemakers are made using coupling of: (i) a plurality of wire contacts 104 from a plurality of wires 106, to (ii) an internal electrical circuitry 402. Specifically, the ceramic structure of pressure sensor capsule 130 is a molded piece, with integral electrical connections of gold, tin or comparable electrical connective material forming internal electrical circuitry 402. These connections pass through the ceramic structure to the location of MEMS pressure sensor 160. In one preferred embodiment of the present invention, the location of the electrical connections to plurality of wire contacts 104 are on the proximal end of pressure sensor capsule 130, which is the end opposite to the end on which isolation diaphragm 150 is located. It should be noted that any suitable type of electrical connections could be used, including an electrical connection made through twisted pair wires, flex circuits, single wires or similar means of electrical connection. In addition, connection between the various electrical contacts described herein may be made through surface solder, solder cups or conductive adhesives. Strain relief 107 may be provided to plurality of wires 106 through application of a flexible RTV. This seal, placed over the conductive connection of wires or flex circuits, provides both strain relief and additional corrosion protection. In another preferred embodiment, a flexible circuit carrying material (flex-circuit) may be used to provide the circuitry needed to connect MEMS pressure sensor 160 to plurality of wires 106. In this embodiment, pressure sensor capsule 130 is separated into two or more pieces, MEMS pressure sensor 160 may be directly mounted on the flexible circuit carrying material and pressure sensor capsule 130 would then be mounted to the flexible circuit carrying material to create a sandwiched, layered construction.

Figure 6:
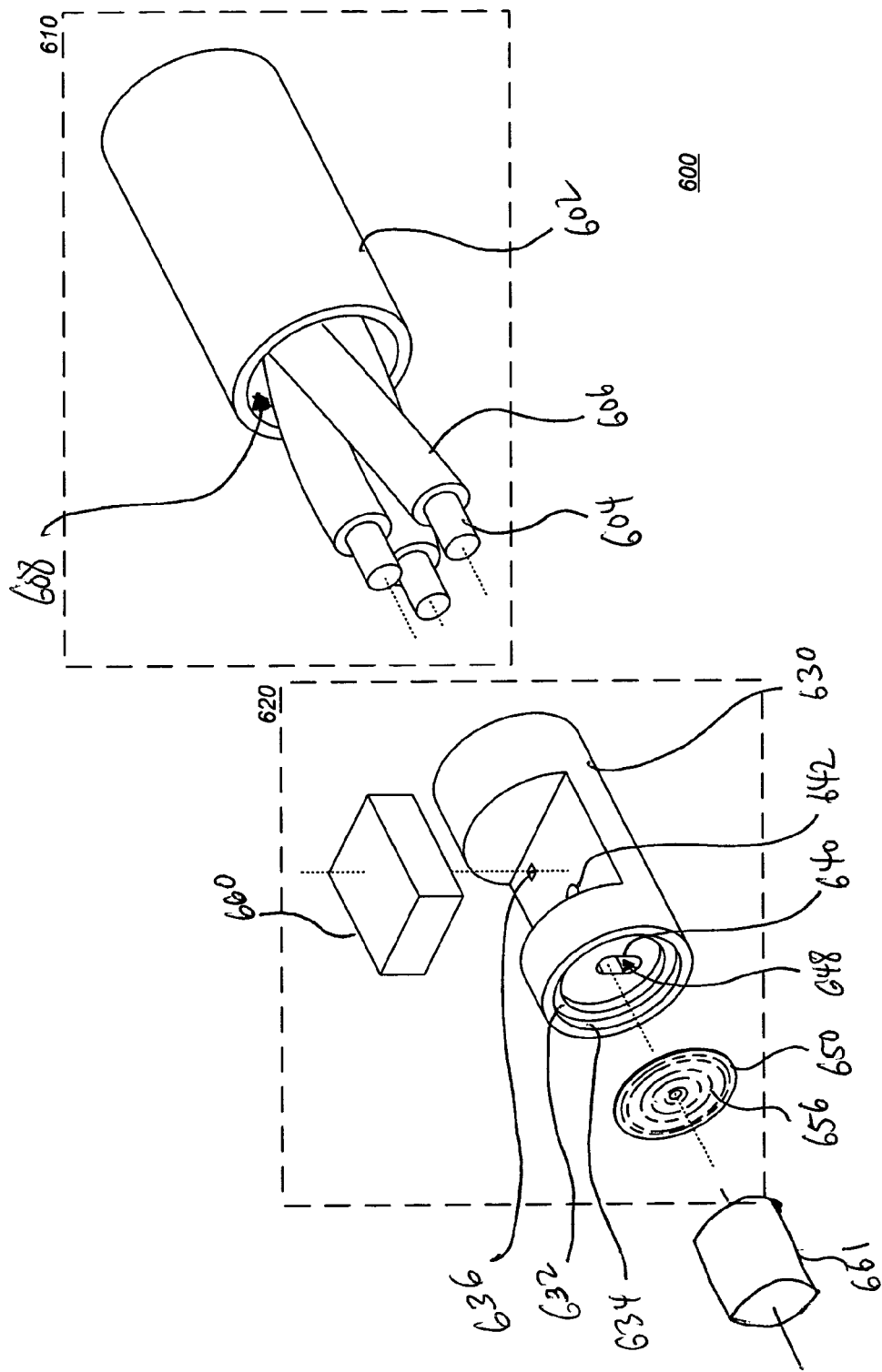
FIG. 6 is a perspective view of a second pressure sensing module configured in accordance with a second preferred embodiment of the present invention.
Figure 7:
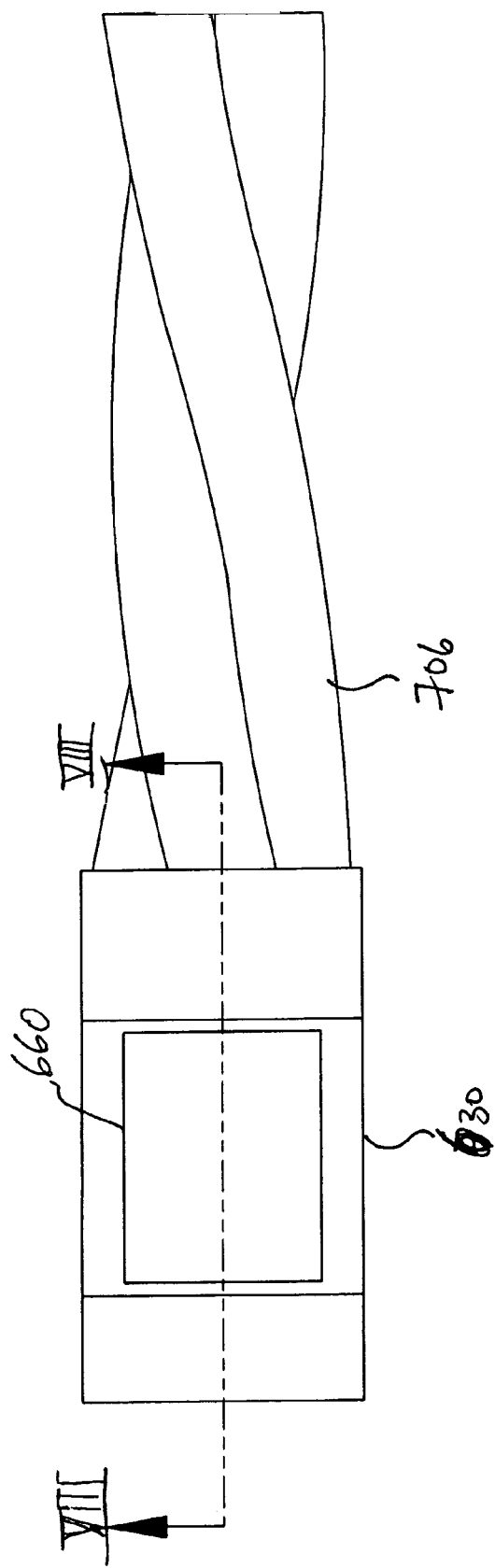
FIG. 7 is a top plan view of the second pressure sensing module of FIG. 6.
Figure 8:
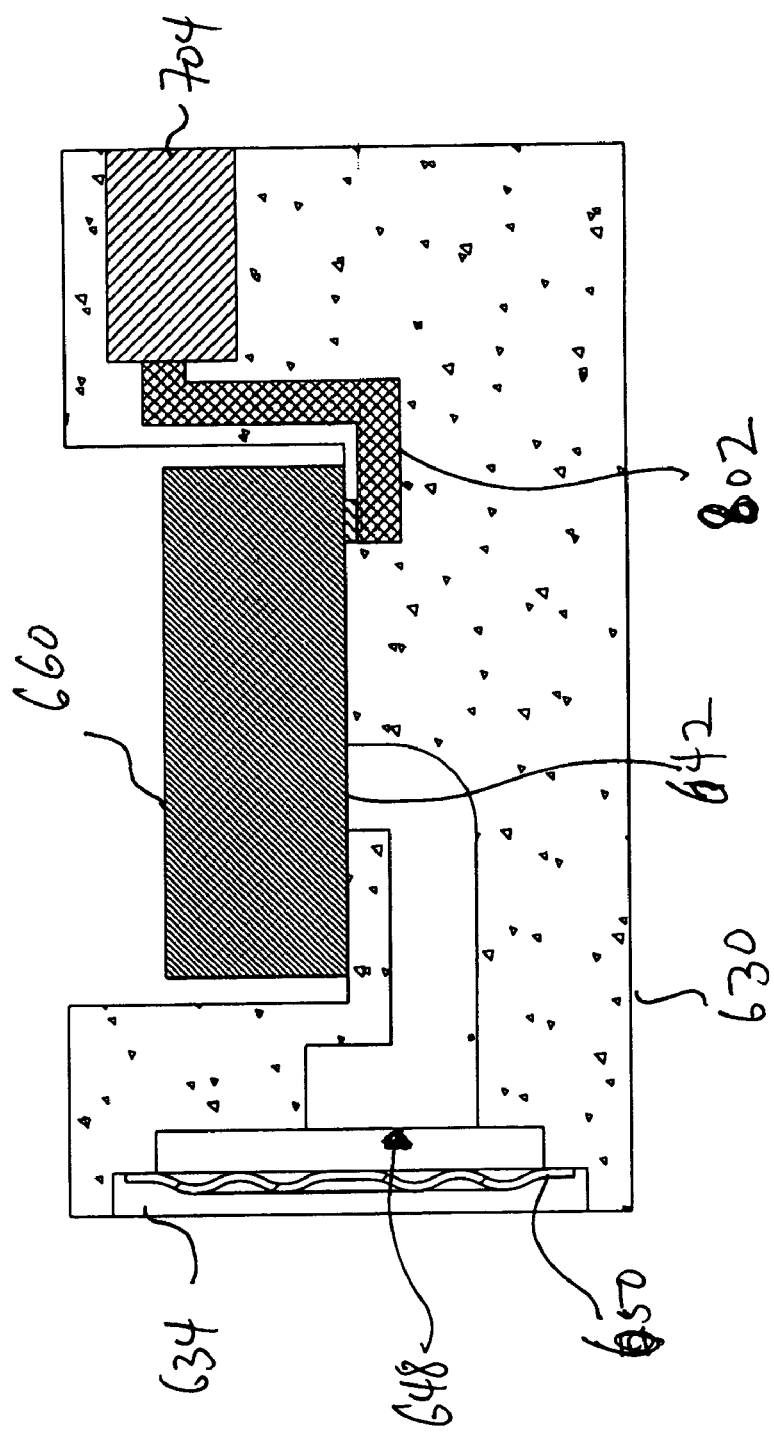
FIG. 8 is a cross-sectional view of the second pressure sensing module of FIG. 6, taken along line VII—VII of FIG. 7.

FIGS. 6–8 illustrate a second pressure sensing module 620 configured in accordance with a second preferred embodiment of the present invention. It should be noted that, unless otherwise noted, the description provided above for the embodiment of the pressure sensing module exemplified by pressure sensing module 120 is equally applicable to this second and other preferred embodiments.

In this embodiment, a pressure sensor 660 is mounted within a cavity 638 in a pressure sensor capsule 630 via a plurality of bump connectors 636. Plurality of bump connectors 636 is connected to a plurality of wire connectors 604 from a plurality of wires 606 via an electrical circuit 802. Once connected, second pressure sensing module 620 may be mounted in interior 608 of a catheter 602

Further, in this embodiment the attachment of an isolation diaphragm 650, which includes a flat border 652, is to a flat surface 632 within a rimmed portion 634 on pressure sensor capsule 630. The pressure from the media to be measured is transferred from isolation diaphragm 650 to pressure sensor 660 through an air filled pressure transfer cavity 648 having a diaphragm-side opening 640 and a sensor-side opening 642. Strain relief at the attachment surface is provided by a plurality of corrugations 656 stamped into the surface of isolation diaphragm 650. Plurality of corrugations 656 also provides extended linearity for larger diaphragm displacement excursion. This design presents a simpler architecture, but does not isolate the adhesive junction between isolation diaphragm 650 to the ceramic structure of pressure sensor capsule 630 nor provide a smooth transition to the outer case. In this embodiment, isolation diaphragm 650 may be made larger, as compared to the top hat design of isolation diaphragm 150 of pressure sensor module 120, to extend its active area to the maximum diameter of the ceramic structure of pressure sensor capsule 630. Like the top hat design described above, isolation diaphragm 650 may be attached to the ceramic structure using adhesives or brazing methods. Further, in this embodiment, isolation diaphragm 650 may be hermetically sealed to catheter tubing 602 through a weld operation and be in an end mount configuration. Isolation diaphragm 650 may also include a protective ring 661 at its tip. Protective ring 661 may be a metal ring or a ring made from an adhesive such as RTV. Thus, isolation diaphragm 650 is located between the outer wall of catheter tubing 602 and protective ring 661.

Figure 9:
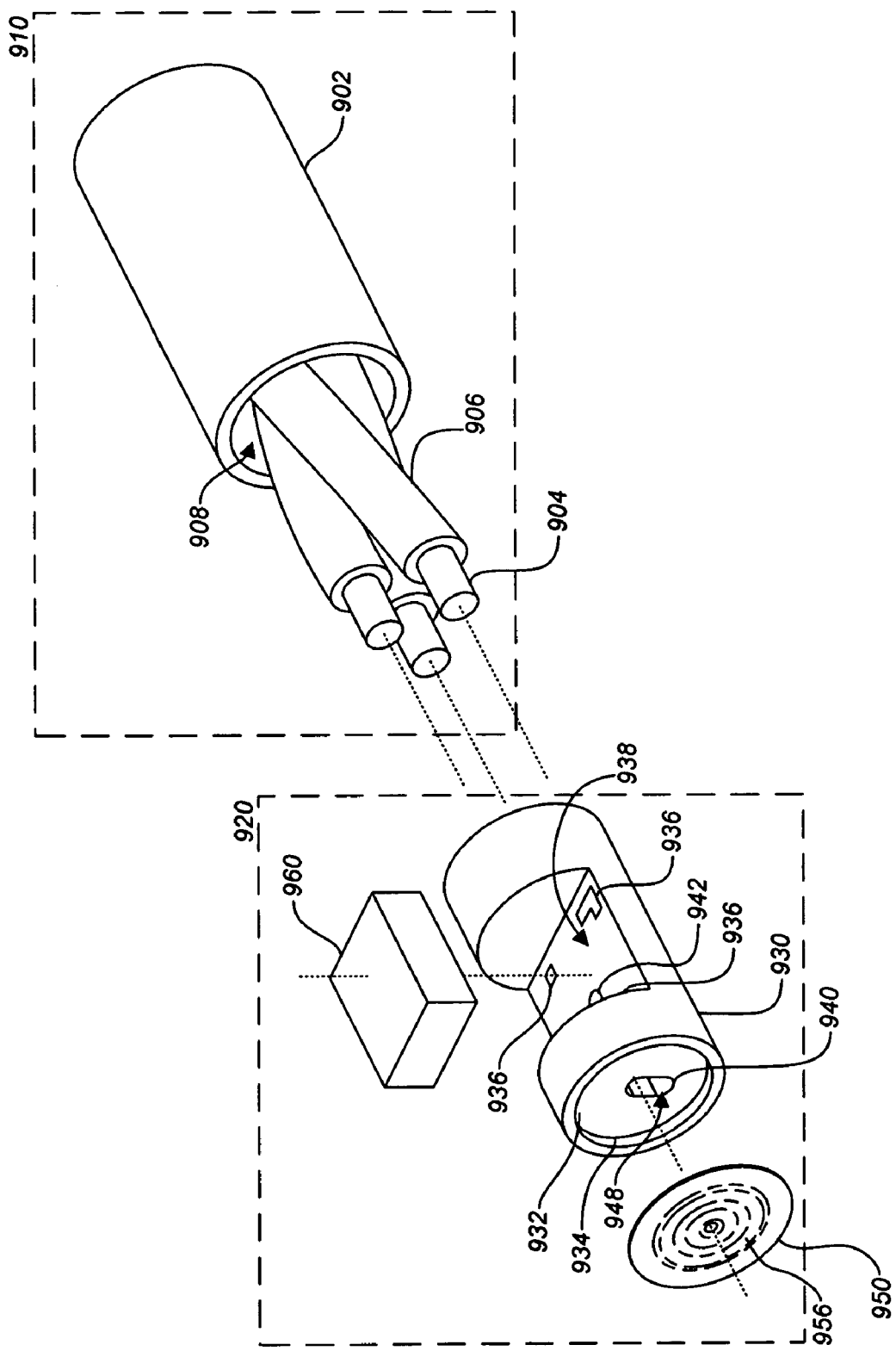
FIG. 9 is a perspective view of a third pressure sensing module configured in accordance with a third preferred embodiment of the present invention.
Figure 10:
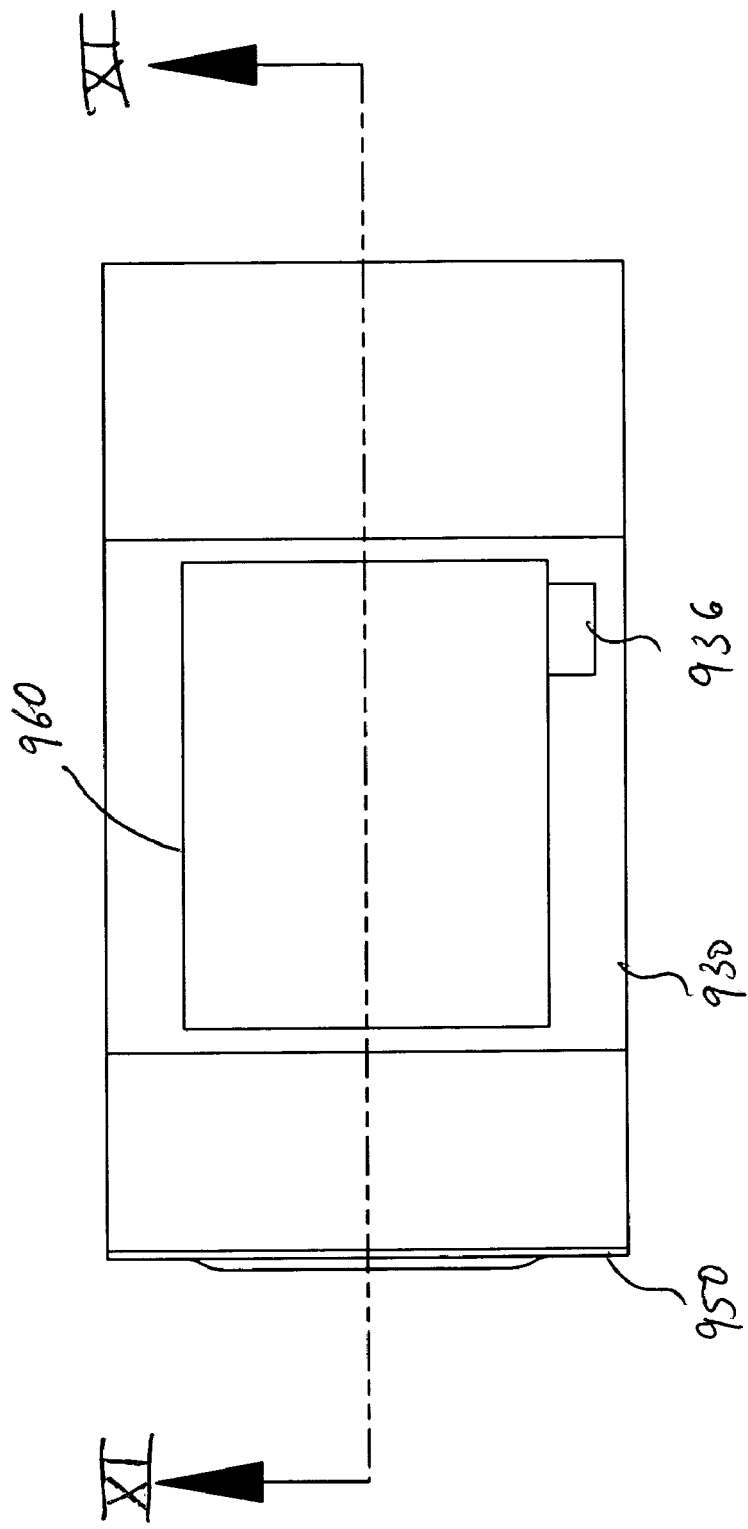
FIG. 10 is a top plan view of the third pressure sensing module of FIG. 9.
Figure 11:
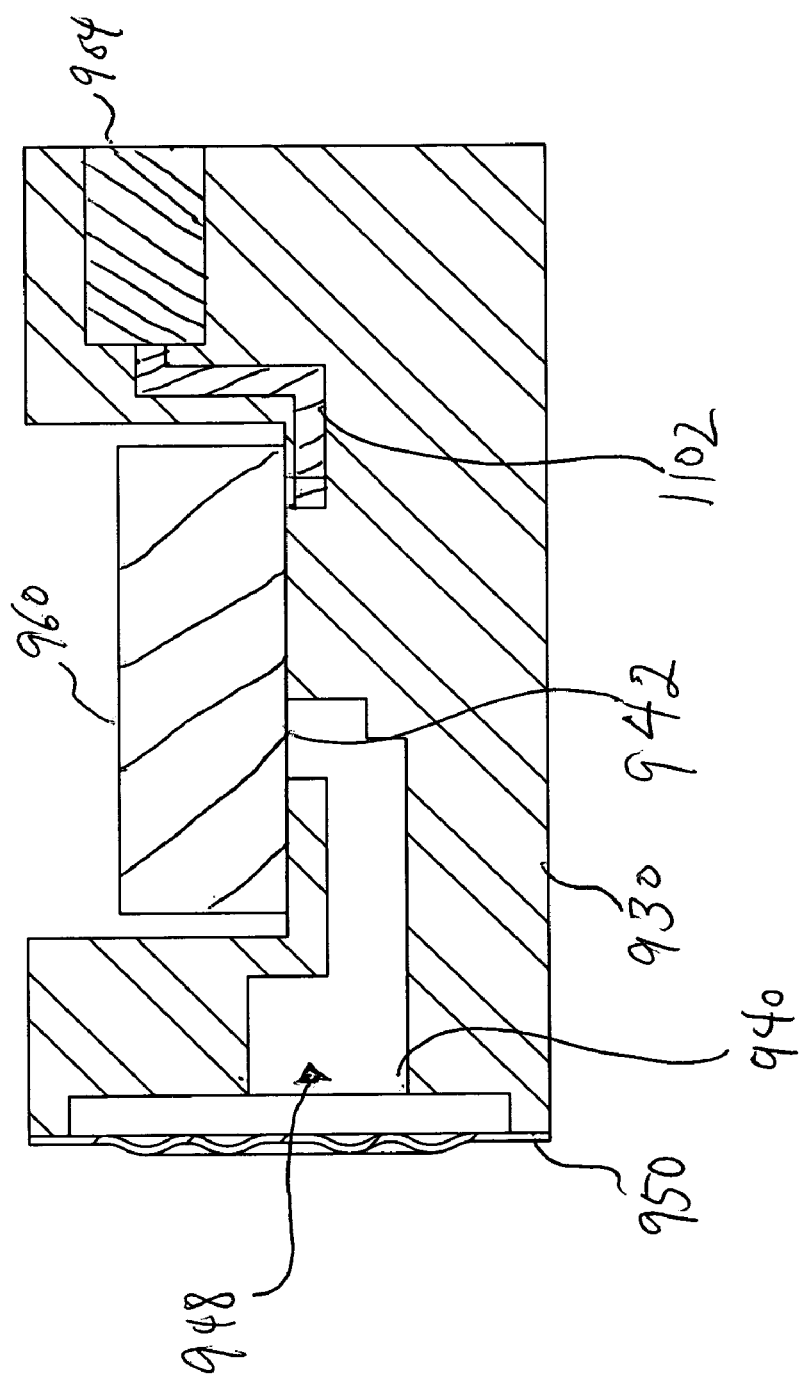
FIG. 11 is a cross-sectional view of the third pressure sensing module of FIG. 9, taken along line XI—XI of FIG. 10.

FIGS. 9–11 illustrate a third pressure sensing module 920 configured in accordance with a third preferred embodiment of the present invention. In this embodiment, a pressure sensor 960 is mounted within a cavity 938 in a pressure sensor capsule 930 via a plurality of bump connectors 936. Plurality of bump connectors 936 is connected to a plurality of wire connectors 904 from a plurality of wires 906 via an electrical circuit 1102. Once connected, third pressure sensing module 920 may be mounted in interior 908 of a catheter 902

In this embodiment, the attachment of an isolation diaphragm 950, which includes a flat border 952, is to a flat ceramic surface 932 on pressure sensor capsule 930. The pressure from the media to be measured is transferred from isolation diaphragm 950 to pressure sensor 960 through an air filled pressure transfer cavity 948 having a diaphragm-side opening 940 and a sensor-side opening 942. Similar to isolation diaphragm 650, stress relief from the attachment surface is provided by a plurality of corrugations 956 stamped into the surface of isolation diaphragm 950. This design, similar to the design described above for second pressure sensing module 620, presents a simple architecture, and allows for the welding of isolation diaphragm 950 to the ceramic structure of pressure sensor capsule 930 because the diameter of isolation diaphragm 950 is as large as the diameter of the ceramic structure.

Figure 12:
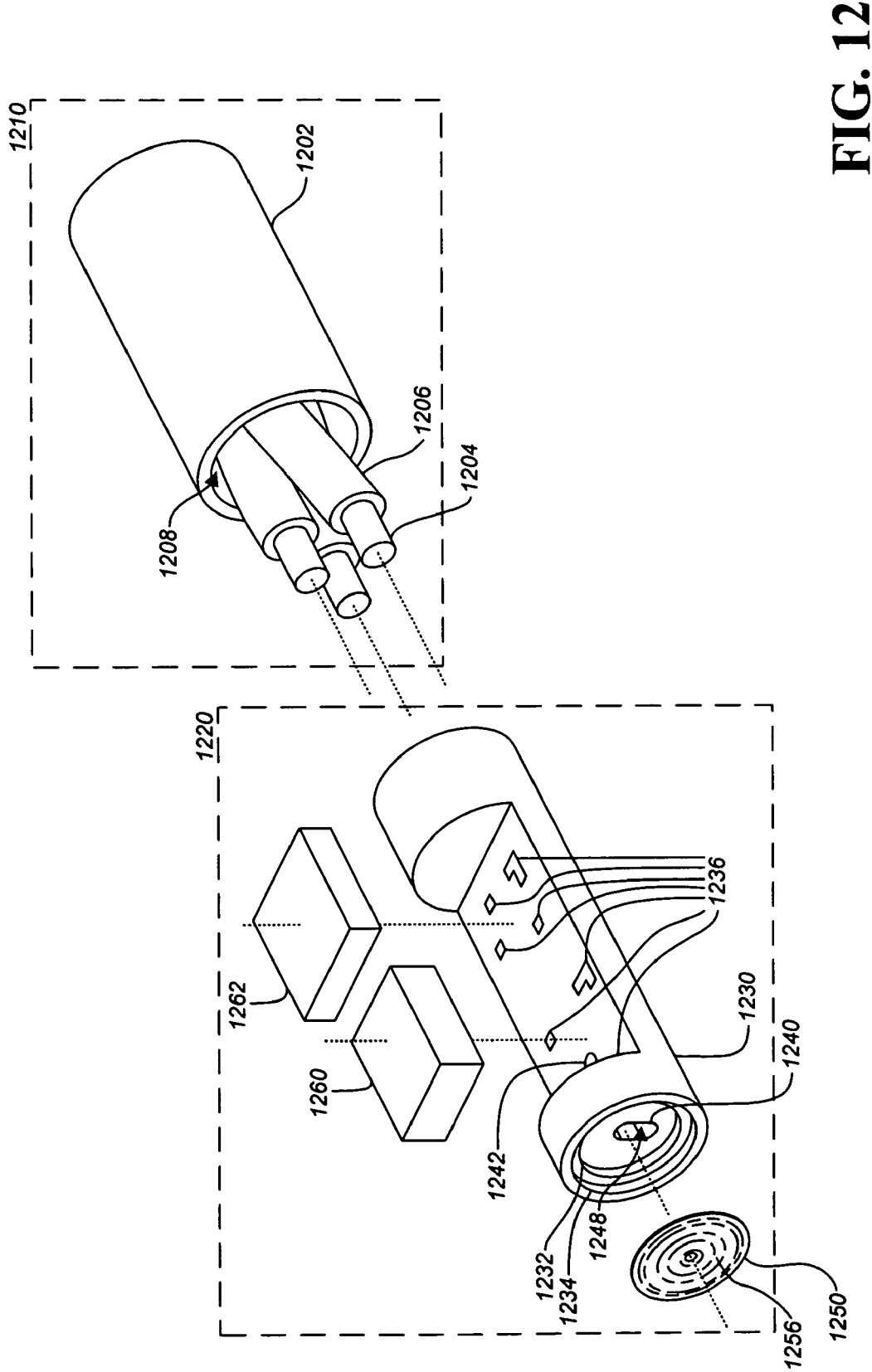
FIG. 12 is a perspective view of a fourth pressure sensing module configured in accordance with a fourth preferred embodiment of the present invention.
Figure 13:
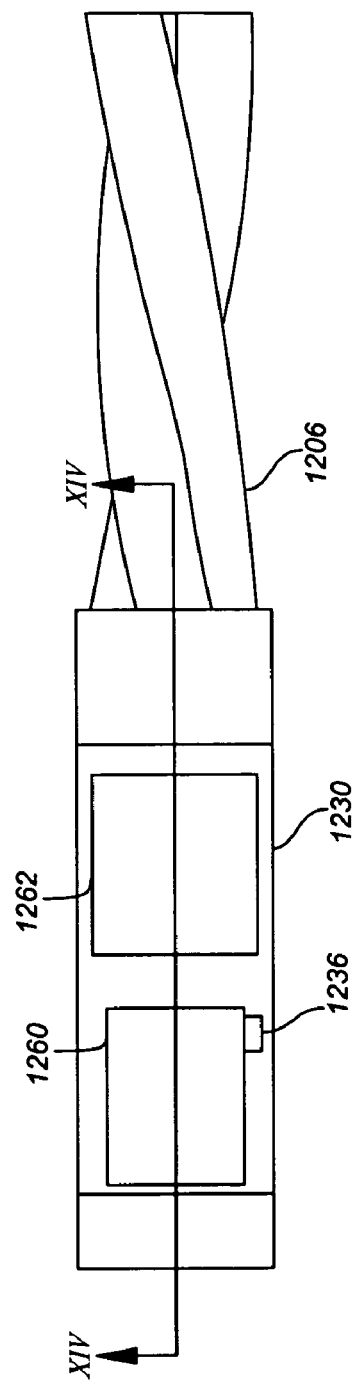
FIG. 13 is a top plan view of the fourth pressure sensing module of FIG. 12.
Figure 14:
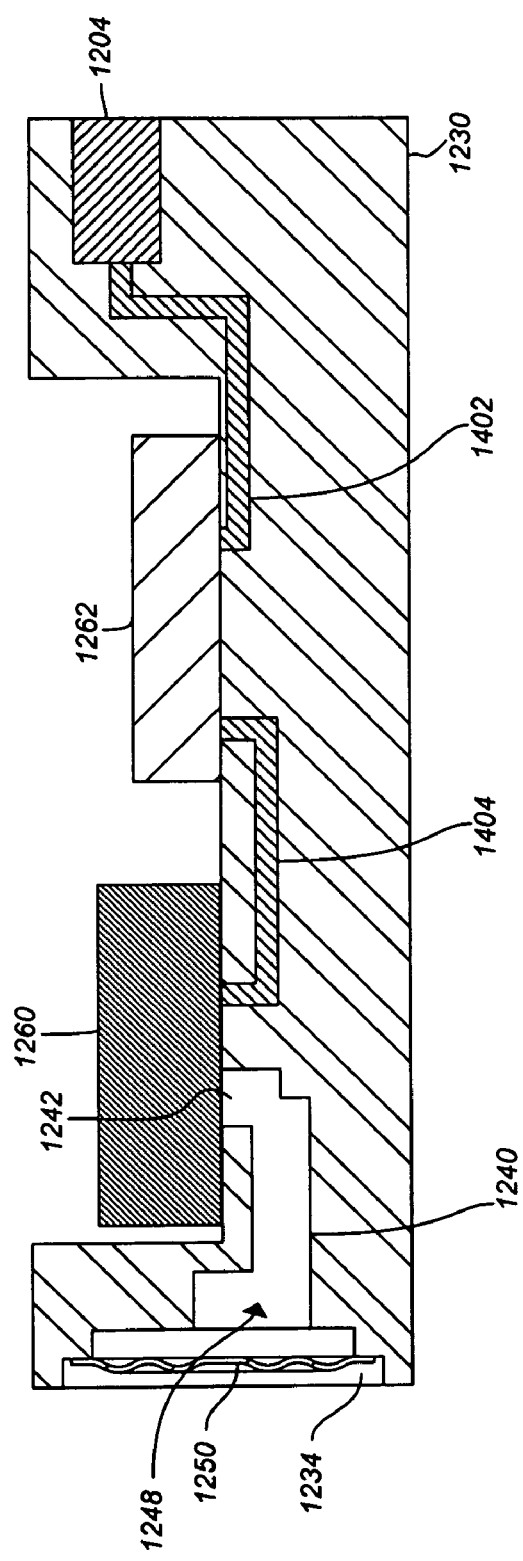
FIG. 14 is a cross-sectional view of the fourth pressure sensing module of FIG. 12, taken along line XIV—XIV of FIG. 13.

FIGS. 12–14 illustrate a fourth pressure sensing module 1220 configured in accordance with a fourth preferred embodiment of the present invention. In this embodiment, a pressure sensor 1260 is mounted within a cavity 1238 in a pressure sensor capsule 1230 via a plurality of bump connectors 1236. Plurality of bump connectors 1236 are connected to a plurality of wire connectors 1204 from a plurality of wires 1206 via an electrical circuit 1402. Further, in this embodiment, instead of confining all the functionality of the pressure sensor into a single die, a separate die 1262 may be included in fourth pressure sensing module 1220 to provide such functionality as additional pre-processing, amplification, further post-processing of the measured signals, or additional sense function (temperature, chemical, & biological). Once pressure sensor 1260 is connected with separate die 1262, fourth pressure sensing module 1220 is then mounted in the interior 1208 of a catheter 1202.

In this embodiment, the attachment of an isolation diaphragm 1250 to pressure sensor capsule 1230 is similar to the connection of isolation diaphragm 652 to pressure sensor capsule 630, as discussed above. In addition, the functioning of pressure sensor capsule 1230 is also similar to pressure sensor module 630, with the exception that pressure sensor capsule 1230 may contain additional functionality, as noted above.

A MEMS pressure sensor device can also be electrically coupled to a pressure sensing module through wire bonds as compared to the use of solder bumps as described for the above embodiments. Because the MEMS pressure sensor device has both its pressure sense diaphragm and electrical circuitry—including contacts for the electrical circuitry—on the same surface of a silicon die, the MEMS pressure sensor device is mounted with its pressure sense diaphragm/contact-side up. The contacts are then wire bonded to contacts on the pressure sensing module. In one preferred embodiment of the present invention, the cavity in which the MEMS pressure sensor is mounted is covered by the isolation diaphragm. Thus, this cavity needs to be sealed to prevent loss of transfer of the pressure affecting isolation diaphragm.

Figure 15:
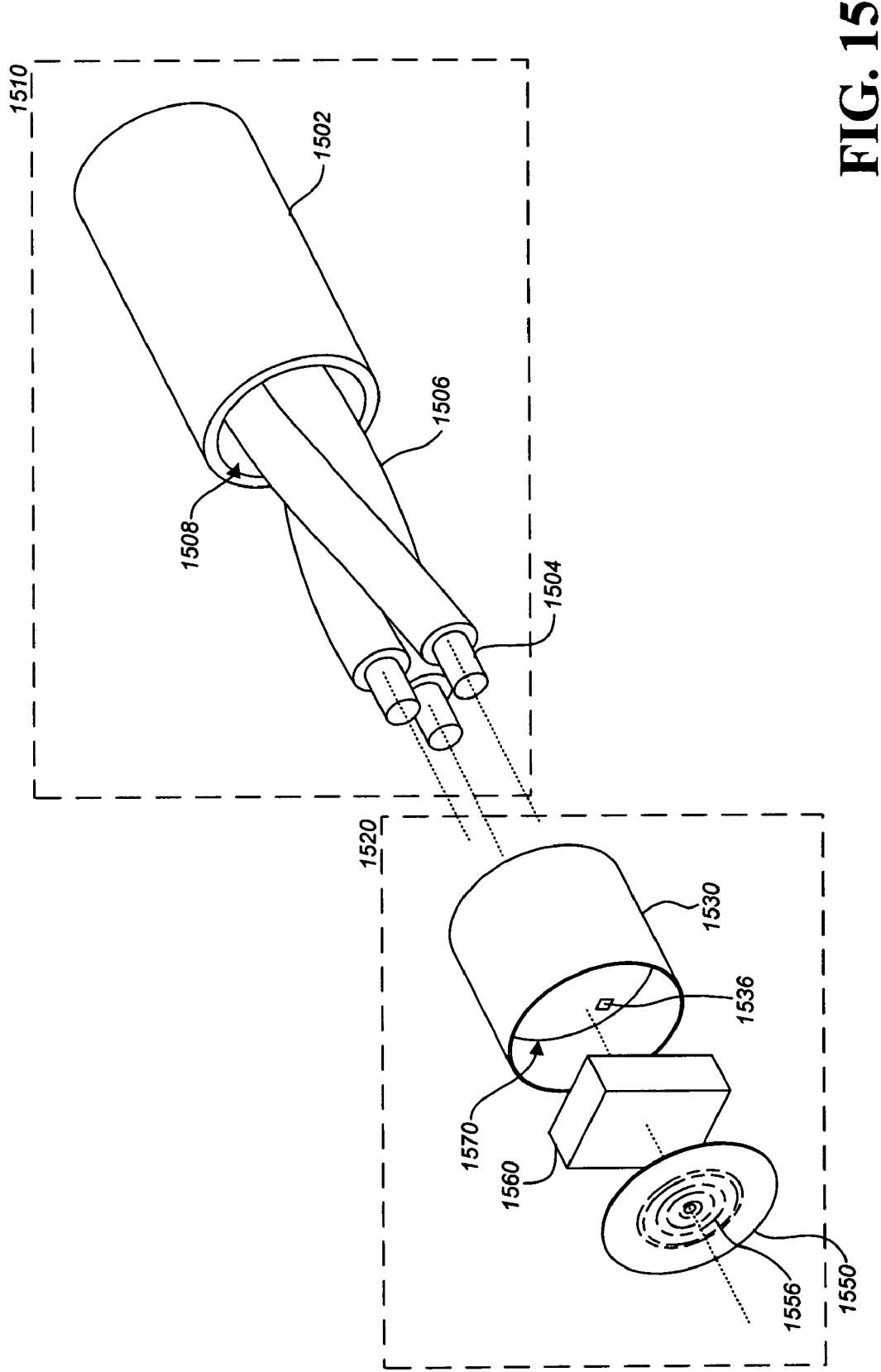
FIG. 15 is a perspective view of a fifth pressure sensing module having a cavity mounted pressure sensor configured in accordance with a fifth preferred embodiment of the present invention.
Figure 16:
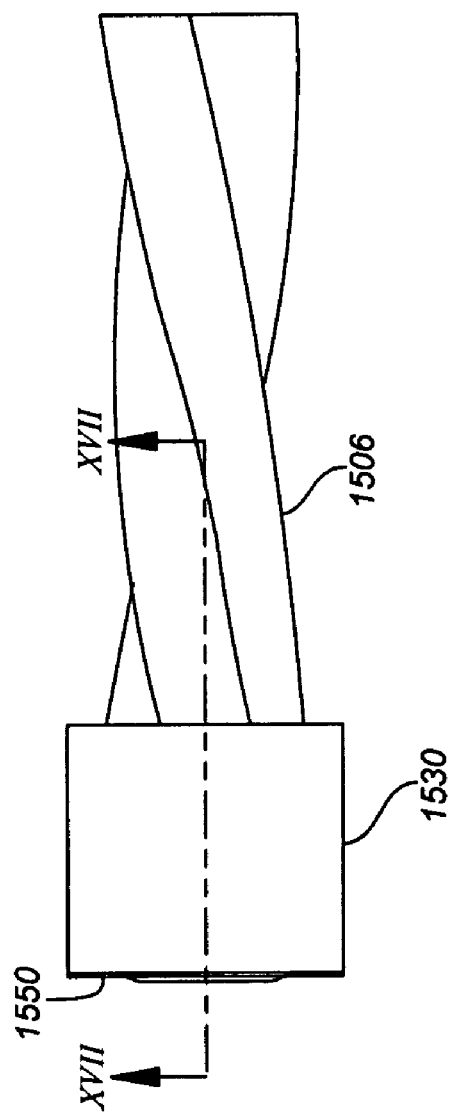
FIG. 16 is a top plan view of the fifth pressure sensing module of FIG. 15.
Figure 17:
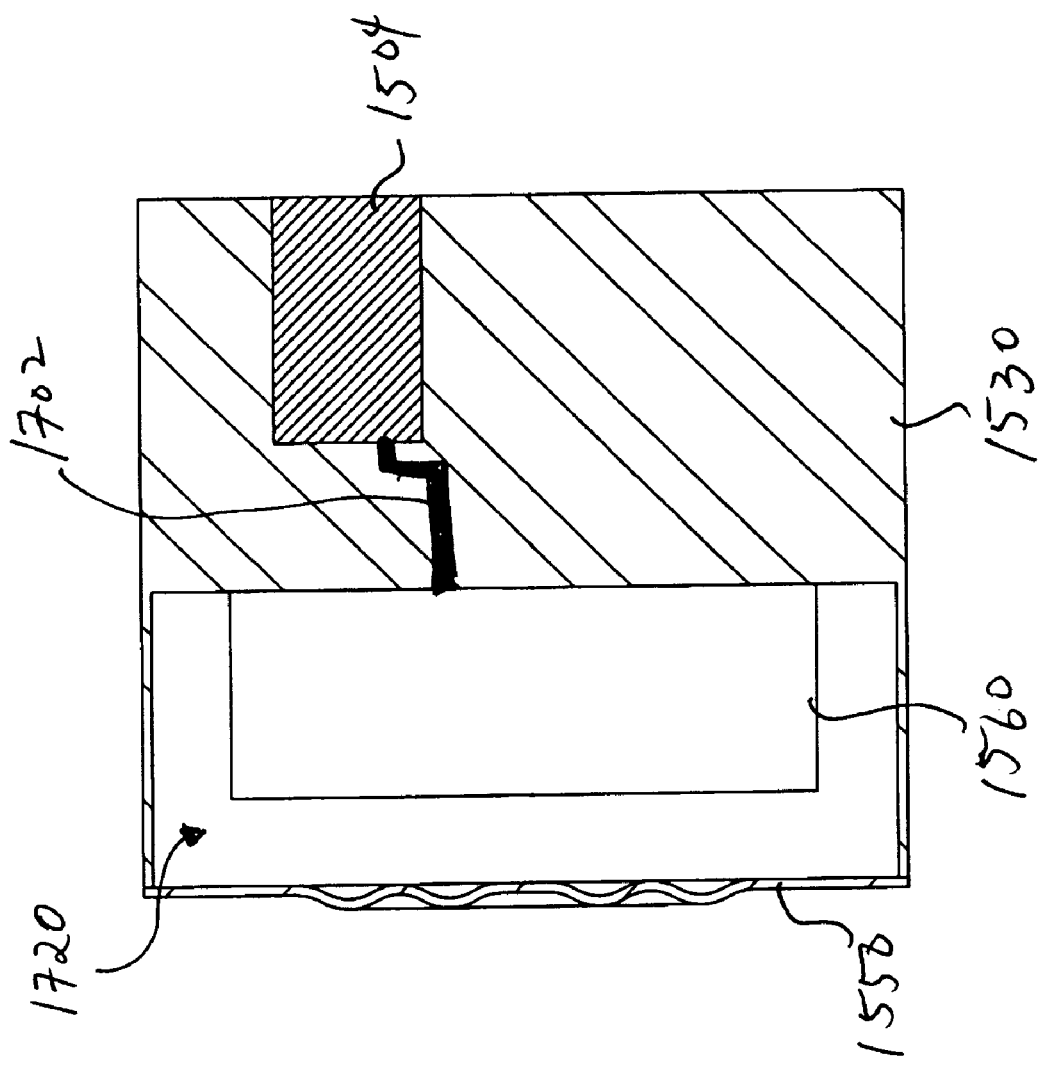
FIG. 17 is a cross-sectional view of the fifth pressure sensing module of FIG. 15, taken along line XVII—XVII of FIG. 16.

FIGS. 15–16 illustrate a fifth pressure sensing module 1520 configured in accordance with a fifth preferred embodiment of the present invention, where a MEMS pressure sensor 1560 is mounted under an isolation diaphragm 1550 within an cavity 1570 of a pressure sensor capsule 1530. This mounting configuration results in a smaller geometry device as neither a separate chamber for mounting MEMS pressure sensor 1560 nor an air pressure transfer cavity for transferring the pressure measured by isolation diaphragm 1550 are required. Further, this configuration also allows for the electrical coupling of MEMS pressure sensor 1560 to a plurality of contacts 1536 using either wire bonds or solder bumps. However, when MEMS pressure sensor 1560 is connected to pressure sensing module 1520 in a solder bumped configuration and an underfill material is used to adhere MEMS pressure sensor 1560, a pressure channel that extends beyond the body of MEMS pressure sensor 1560 should be provided. This is because the side of MEMS pressure sensor 1560 on which sense diaphragm is located is both facing down and layered between the body of MEMS pressure sensor 1560 and pressure sensing module 1520. The pressure channel provides a coupling of the pressure from isolation diaphragm 1550 through the underfill material to the sensing diaphragm of MEMS pressure sensor 1560. Similar to the other embodiments described herein, to connect MEMS pressure sensor 1560 to an external device, a plurality of electrical connections 1702 are passed through to the proximal end of the ceramic body of pressure sensor capsule 1530, as illustrated in FIG. 17. These electrical connections contact a plurality of wire contacts 1504 belonging to a plurality of wires 1506 in a catheter tubing 1502.

Figure 20:
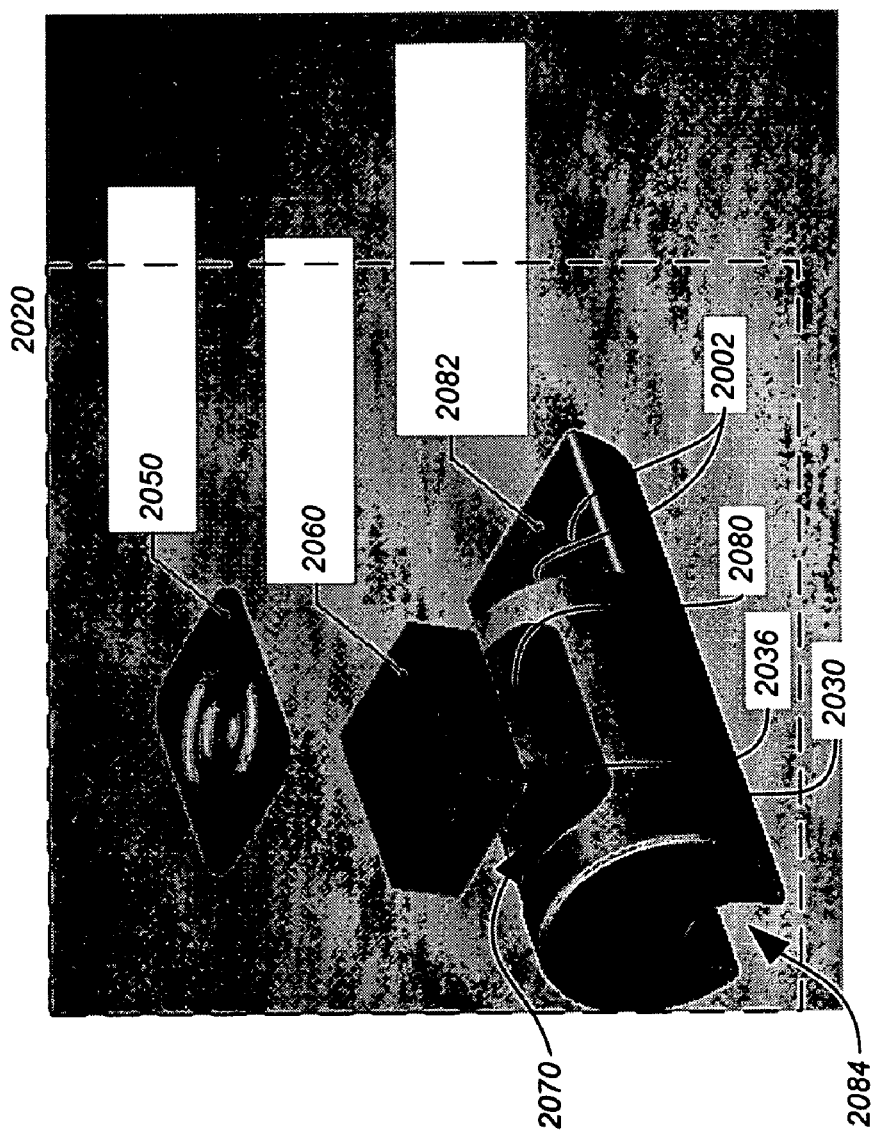
FIG. 20 is a perspective view of a sixth pressure sensing module having a side-mounted pressure sensor configured in accordance with a sixth preferred embodiment of the present invention.
Figure 21:
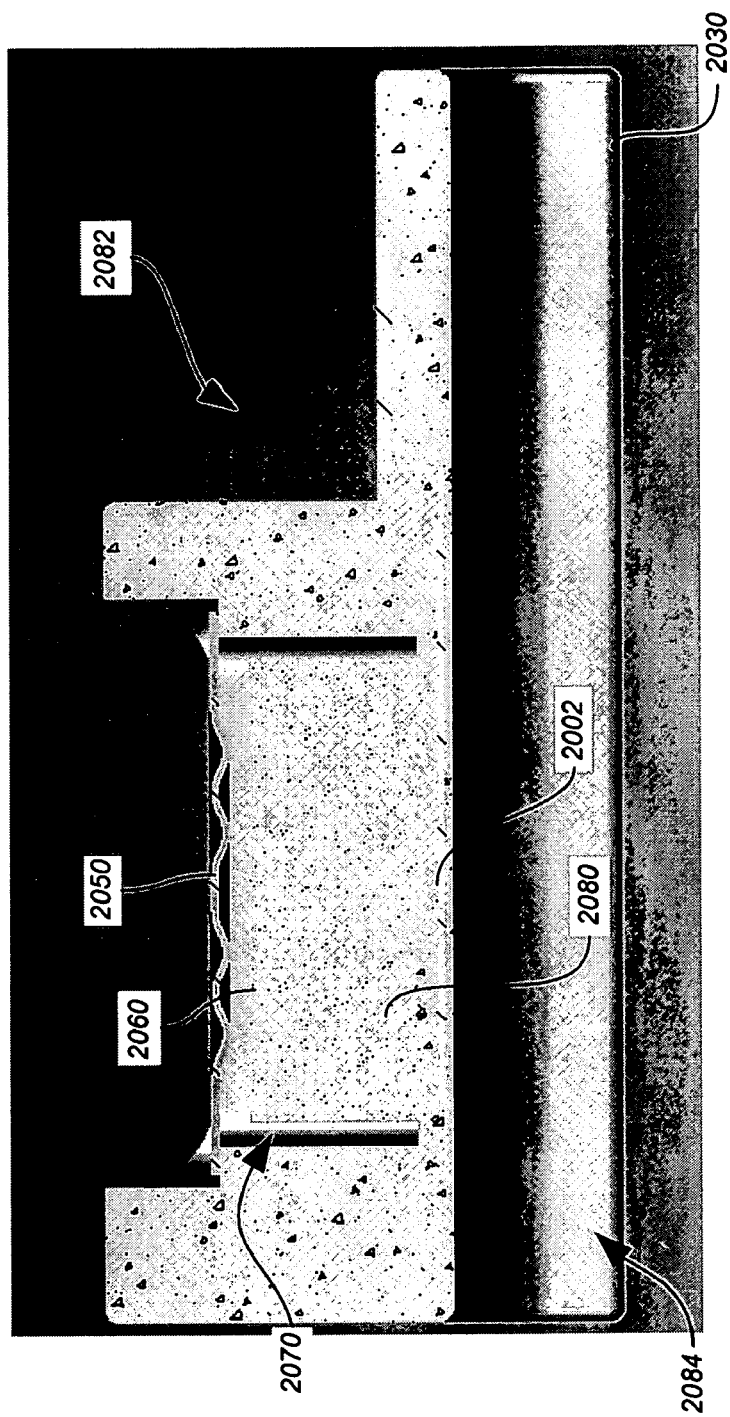
FIG. 21 is a cross-sectional view of the sixth pressure sensing module of FIG. 20, taken along line XVII—XVII of FIG. 16; and, FIG. 22 is a block diagram of a pressure sensor system configured in accordance with one embodiment of the present invention in which the pressure sensing modules described herein may be used.

FIGS. 20–21 illustrate a sixth pressure sensing module 2020, configured in accordance with a sixth preferred embodiment of the present invention, where a MEMS pressure sensor 2060 is mounted within a cavity 2070 of a pressure sensor capsule 2030 to implement a side-mounted pressure sensor. Cavity 2070 is displaced on the side of pressure sensor capsule 2030, and an isolation diaphragm is 2050 is mounted on a ledge 2080. This configuration does not require a separate cavity nor air pressure transfer chamber and allows for the MEMS pressure sensor 2060 to be electrically coupled to a plurality of contacts 2036 using either wire bond connections or a plurality of bumps, as discussed for MEMS pressure sensor 1560 of fifth pressure sensing module 1520. A plurality of electrical connections 2002, located in a notched portion 2082 of the body at the proximal end of pressure sensing capsule 2030 is used to contact a plurality of wire contacts from a plurality of wires in a catheter or lead for an external device (not shown). In one preferred embodiment, the plurality of wire contacts are soldered onto plurality of electrical connections 2002.

By mounting isolation diaphragm 2050 on the side of pressure sensing capsule 2030, a slot, or wire channel, 2084 may be created in pressure sensing capsule 2030 to allow wires or other leads (such as pacing leads) to pass beneath pressure sensing capsule 2030. These wires may include wires for other devices mounted downstream of the distal end of pressure sensing capsule 2030 on the catheter tubing. In one preferred embodiment, pressure sensing capsule 2030 is mounted on the end of the catheter tubing, and any leads may extend through slot 2084. In another embodiment, the body of pressure sensing capsule 2030 may be completely enclosed in the catheter tubing, which will have a cut-out for isolation diaphragm 2050.

Figure 18:
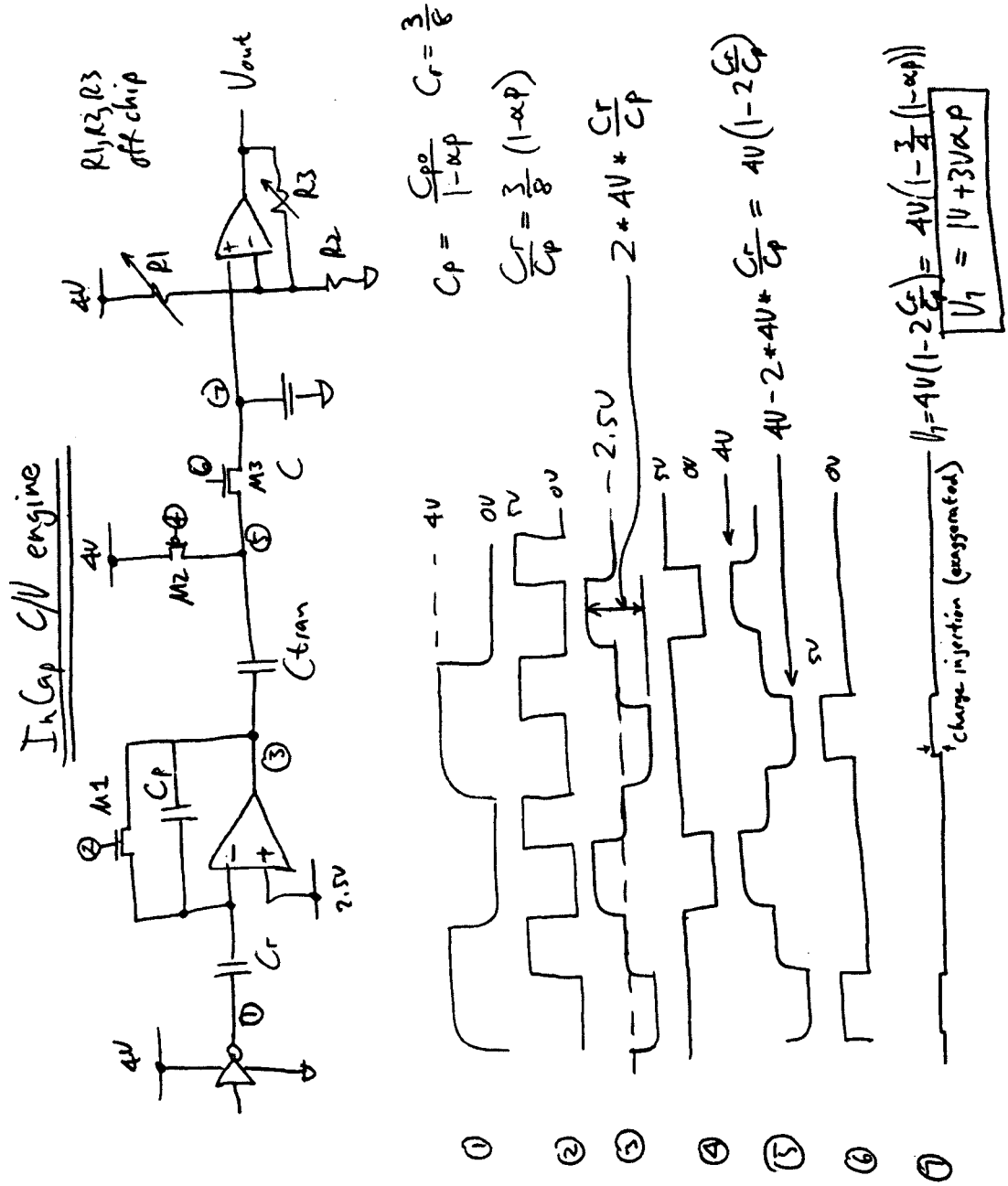
FIG. 18 is an electronics block diagram of the sensing portion of the MEMS pressure sensor configured in accordance with one preferred embodiment of the present invention.

In one preferred embodiment, as shown in FIG. 18, the MEMS pressure sensors described herein includes a circuit 1800 containing both a sensing capacitor (Cp) and a reference capacitor (Cr). Pressure changes sensed by isolation diaphragm 150 will cause changes in the sensing capacitor Cp. This variation in capacitance is amplified by an Op-Amp in circuit 1800. Circuit 1800 converts the capacitive pressure sensed into a signal, which in one embodiment is a pulse width modulated (PWM) digitally coded signal for a range of voltages (e.g. 0.5 to 4.5 volts) that represents the sensed pressure.

Figure 19:
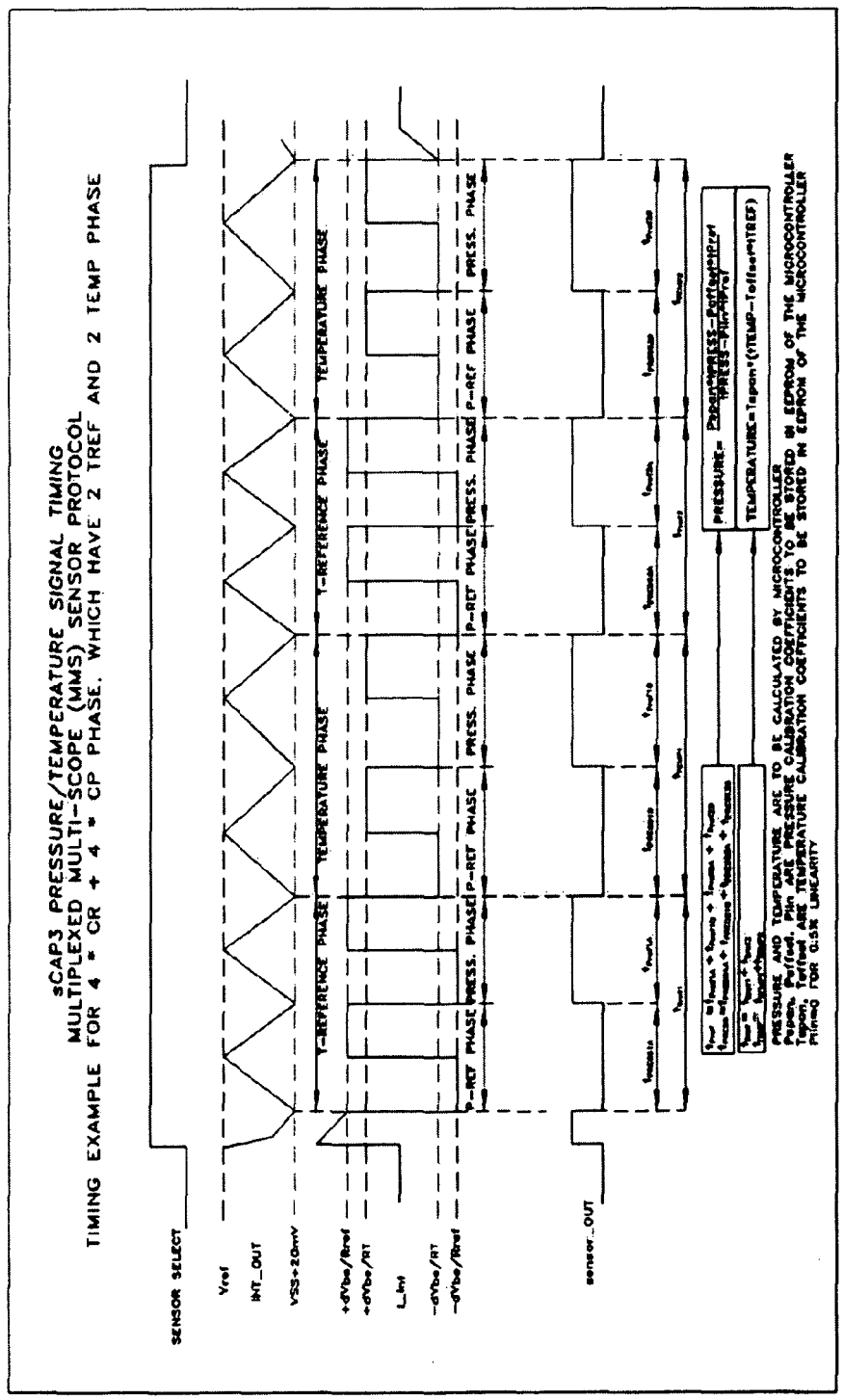
FIG. 19 is a signal timing chart of the MEMS pressure sensor of FIG. 18.

As illustrated in FIG. 19, in one preferred embodiment the digital output is pulse width modulated. The communications is initiated with a marker pulse of a specific length. This is followed by a null pulse of predefined level (a logical one or zero). The pulse width temperature signal is transmitted, with a predefined minimum and maximum width proportional to a minimum and maximum temperature. This is followed by a second null pulse. The pressure signal is transmitted next with a minimum and maximum pulse width proportional to pressure. The sequence is then repeated. In other embodiments, digital output methods such as pressure only, re-sequenced timing, coded digital signals, Frequency Shift Keyed (FSK), and Pulse Amplitude Coded (PAC) signals can be used.

Figure 22:
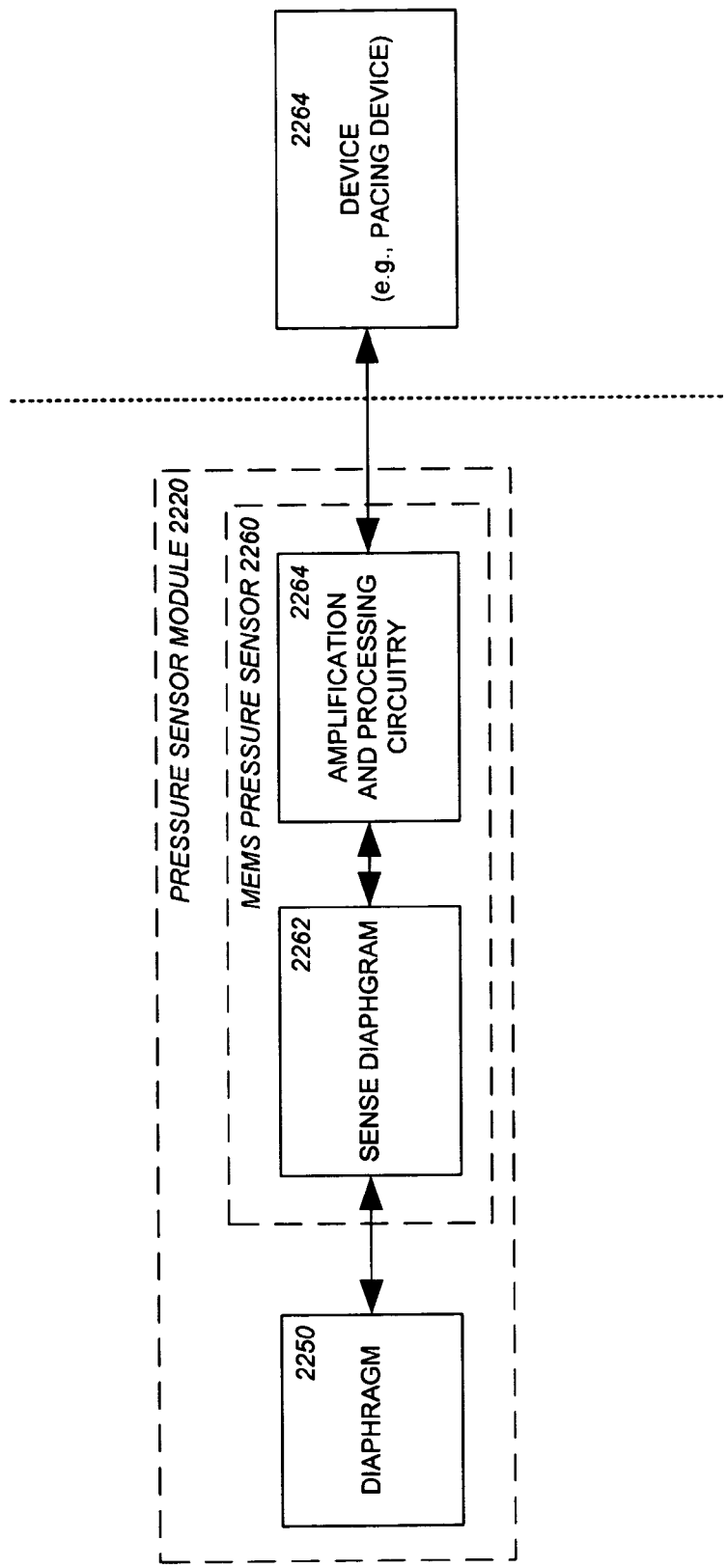

FIG. 22 illustrates one exemplary application of the pressure sensor modules described herein, where a pressure sensor module 2220, which includes a diaphragm 2250 configured similarly to the isolations diaphragms described above is coupled to a sense diaphragm 2262 in a MEMS pressure sensor 2260. An amplification and processing circuitry 2264 reads the signals from sense diaphragm 2262, and after processing them, delivers the processed signals to a device 2264. For example, device 2264 may be a pacing device. Device 2264 may have other wires for use in providing pacing that are not shown in the figure, but which may be integrated into the lead in which pressure sensor module 2220 is mounted.

The MEMS pressure sensor of the present invention provides the following features:

1. Accuracy: MEMS devices are micro-machined structures controlled through precise physical and chemical attributes. The accuracy achieved from using these techniques provide highly accurate reproduction and consistency.

2. Parasitic effects: Since the MEMS capacitive sensing diaphragm is integrated with the sensing detector and amplifier, the parasitic wiring connection is eliminated or rendered insignificant.

3. Stability: The MEMS system utilizes a combination reference diaphragm and sensing diaphragm. The ratio of the two elements reduces manufacturing variations, long-term drift and thermal effects.

4. Material fatigue-based drift: The MEMS silicon structure shows insignificant drift with time as compared to metal diaphragm and wired interconnect.

The embodiments described above are exemplary embodiments. Those skilled in the art may now make numerous uses of, and departures from, the above-described embodiments without departing from the inventive concepts disclosed herein. Various modifications to these embodiments may be readily apparent to those skilled in the art, and the generic principles defined herein may be applied to other embodiments. Thus, the scope of the invention is not intended to be limited to the embodiments shown herein but is to be accorded the widest scope consistent with the principles and novel features disclosed herein. The word "exemplary" is used exclusively herein to mean "serving as an example, instance, or illustration." Any embodiment described herein as "exemplary" is not necessarily to be construed as preferred or advantageous over other embodiments. Accordingly, the present invention is to be defined solely by the scope of the following claims.

What is claimed is:

1. A pressure sensing module comprising:
a pressure sensing capsule having:
a body with a distal end and a proximal end;
an electrical circuit integrated into the body;
a first cavity located between the distal end and the proximal end;
an isolation diaphragm coupled to the distal end of the body of the pressure sensing capsule;
a MEMS pressure sensor mounted within the first cavity of the body of the pressure sensing capsule; and,
a sealed cavity configured to transfer a pressure applied to the isolation diaphragm to the MEMS pressure sensor.

2. The pressure sensing module of claim 1, wherein the body includes a longitudinal axis defined by the distal end and the proximal end, further comprising a wire channel parallel to the longitudinal axis.

3. The pressure sensing module of claim 1, wherein the distal end of the body further comprises a protruding portion, and the isolation diaphragm is shaped to cap the protruding portion.

4. The pressure sensing module of claim 3, wherein the protruding portion of the body comprises a step circumferentially around the protruding portion, and the isolation diaphragm comprises a lip mated to the step.

5. The pressure sensing module of claim 1, wherein the body further comprises a first opening facing the isolation diaphragm on the distal end of the body and a second opening facing the first cavity on the proximal end of the body, the sealed cavity communicating the pressure applied to the isolation diaphragm to the MEMS pressure sensor through the sealed cavity.

6. The pressure sensing module of claim 1, wherein the sealed cavity is filled with a liquid.

7. The pressure sensing module of claim 6, wherein the liquid comprises an incompressible liquid.

8. The pressure sensing module of claim 7, wherein the incompressible liquid comprises silicon oil.

9. The pressure sensing module of claim 1, wherein the pressure sensing capsule comprises a liquid fill channel in communication with sealed cavity.

10. The pressure sensing module of claim 1, wherein the isolation diaphragm comprises a plurality of corrugations.

11. The pressure sensing module of claim 8, wherein the plurality of corrugations are concentric.

12. The pressure sensing module of claim 8, wherein the plurality of corrugations provide linear operation over a larger diaphragm displacement.

13. The pressure sensing module of claim 1, further comprising a plurality of electrical connectors on the proximal end of the body coupled to the electrical circuit.

14. The pressure sensing module of claim 1, further comprising a second sensor mounted in the first cavity, the second sensor being coupled to the MEMS pressure sensor.

15. The pressure sensing module of claim 1, further comprising a temperature sensor.

16. The pressure sensing module of claim 1, wherein the body comprises an embedded connector used to hold a MEMS sensor in contact with the sealed cavity.

17. The pressure sensing module of claim 1, wherein the body is a ceramic substrate comprising embedded connectors used to hold a MEMS sensor in contact with the sealed cavity and in contact with the electrical circuit embedded into the body to pass electrical signals from the MEMS sensor to the electrical circuit.

18. A pressure sensing capsule comprising:
a body with a distal end and a proximal end;
an electrical circuit embedded into the body;
a first cavity located between the distal end and the proximal end;
an isolation diaphragm coupled to the distal end of the body;
a MEMS pressure sensor mounted in the first cavity of the body of the pressure sensing capsule; and,
a pressure transfer cavity having a first opening operatively in communication with the isolation diaphragm and a second opening operatively in communication with the MEMS pressure sensor, the pressure transfer cavity transferring a pressure applied at the isolation diaphragm to the MEMS pressure sensor by transferring the pressure applied from the first opening to the second opening.

19. The pressure sensing capsule of claim 18, wherein the sealed cavity is filled with a liquid.

20. The pressure sensing capsule of claim 19, wherein the liquid comprises an incompressible liquid.

21. The pressure sensing capsule of claim 19, wherein the liquid comprises silicon oil.

22. The pressure sensing capsule of claim 18, wherein the body further comprises a liquid fill channel in communication with the pressure transfer cavity.

23. The pressure sensing capsule of claim 18, wherein the body includes a longitudinal axis defined by the distal end and the proximal end, further comprising a wire channel parallel to the longitudinal axis.

24. The pressure sensing capsule of claim 18, wherein the isolation diaphragm comprises a plurality of corrugations.

25. The pressure sensing capsule of claim 24, wherein the plurality of corrugations are concentric.

26. The pressure sensing capsule of claim 24, wherein the plurality of corrugations provide linear operation of the MEMS pressure sensor over a larger diaphragm displacement.

27. The pressure sensing capsule of claim 18, wherein the body includes a center axis running from the distal end to the proximal end and the first cavity is offset from the center axis.

28. The pressure sensing capsule of claim 18, wherein the body comprises a three-dimensional structure including embedded connectors used to hold the MEMS pressure sensor in contact with the pressure transfer cavity and to pass electrical signals between the MEMS pressure sensor and the electrical circuit.

29. The pressure sensing capsule of claim 28, wherein the three dimensional structure comprises a ceramic substrate.

30. The pressure sensing capsule of claim 18, wherein the isolation diaphragm has a diaphragm center and the first opening has a first opening center, and the first opening center is offset from the center of the diaphragm.

31. The pressure sensing capsule of claim 18, further comprising a lead having a first interior dimension sized to hold the body.

32. The pressure sensing capsule of claim 31, wherein the lead comprises a catheter tubing.

33. The pressure sensing capsule of claim 31, wherein the lead comprises a pacing lead.

34. A method for creating a pressure sensing capsule comprising:
providing a body with a distal end and a proximal end, the body having a first cavity located between the distal end and the proximal end, an electrical circuit embedded into the body, and a pressure transfer cavity having a first opening operatively in communication with the isolation diaphragm and a second opening operatively in communication with the MEMS pressure sensor;

coupling an isolation diaphragm to the distal end of the body;

sealing the isolation diaphragm around the first opening; and, sealing the MEMS pressure sensor to the second opening;

wherein the first opening is operatively in communication with the isolation diaphragm and the second opening is operatively in communication with the MEMS pressure sensor.

35. The method of claim 34, wherein the body includes a liquid fill channel in communication with the pressure transfer cavity, and the method further comprising filling the pressure transfer cavity with the liquid through the liquid fill channel after the isolation diaphragm is sealed around the first opening.

36. The method of claim 35, wherein filling the pressure transfer cavity with a liquid after the isolation diaphragm is sealed around the first opening comprises filling the pressure transfer cavity with the liquid after the MEMS pressure sensor is sealed to the second opening.

37. The method of claim 35, wherein filling the pressure transfer cavity with a liquid after the isolation diaphragm is sealed around the first opening comprises filling the pressure transfer cavity with an incompressible liquid.

38. The method of claim 35, further comprising sealing the liquid fill channel after the pressure transfer cavity is filled with the liquid.

39. The method of claim 34, wherein the body includes a longitudinal axis running from the distal end to the proximal end and providing the body comprises providing the body with a wire channel running parallel to the longitudinal axis.

40. The method of claim 34, wherein a plurality of connectors are displaced within the first cavity of the body and a plurality of solder bumps are displaced on a first surface of the MEMS sensor and mounting the MEMS pressure sensor in the first cavity of the body comprises soldering the plurality of solder bumps on the MEMS pressure sensor to the plurality of connectors within the first cavity of the body.

41. The method of claim 34, wherein sealing the isolation diaphragm around the first opening comprises gluing the isolation diaphragm to the body.

42. The method of claim 41, wherein the distal end of the body comprises a protrusion and the isolation diaphragm comprises a lip portion and gluing the isolation diaphragm to the body comprises gluing the lip portion of the isolation diaphragm to the protrusion.

43. The method of claim 34, wherein sealing the isolation diaphragm around the first opening comprises creating a hermetic seal between the isolation diaphragm and the first opening.

44. The method of claim 34, wherein sealing the MEMS pressure sensor to the second opening comprises creating a hermetic seal between the MEMS pressure sensor and the second opening.

* * * * *